(12) United States Patent
Beach et al.

(10) Patent No.: US 6,566,054 B1
(45) Date of Patent: *May 20, 2003

(54) CYCLIN DEPENDENT KINASE MUTANTS, AND DIAGNOSTIC AND THERAPEUTIC USES RELATED THERETO

(75) Inventors: David H. Beach, Huntington Bay, NY (US); Manuel Serrano, Mill Neck, NY (US)

(73) Assignee: Cold Spring Harbor Laboratory, Cold Spring Harbor, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 564 days.

This patent is subject to a terminal disclaimer.

(21) Appl. No.: 08/706,322

(22) Filed: Aug. 30, 1996

Related U.S. Application Data

(63) Continuation-in-part of application No. 08/581,918, filed on Jan. 2, 1996, now Pat. No. 6,043,030, which is a continuation-in-part of application No. 08/497,214, filed on Jun. 30, 1995, now Pat. No. 6,331,390, which is a continuation-in-part of application No. 08/346,147, filed on Nov. 22, 1994, now Pat. No. 5,435,551, which is a continuation-in-part of application No. 08/306,511, filed on Sep. 14, 1994, now Pat. No. 5,962,316, which is a continuation-in-part of application No. 08/248,812, filed on May 25, 1994, now Pat. No. 5,889,169, which is a continuation-in-part of application No. 08/227,371, filed on Apr. 14, 1994, which is a continuation-in-part of application No. 08/154,915, filed on Nov. 18, 1993.

(51) Int. Cl.$^7$ .................................................. C12Q 1/68
(52) U.S. Cl. ............................ 435/6; 435/7.1; 435/7.72
(58) Field of Search ........................... 435/6, 7.1, 7.72, 435/14, 172.1; 935/74, 77, 78

(56) References Cited

PUBLICATIONS

Serrano et al "A New Regulatory Motif in Cell Cycle Control Causing Specific Inhibition of Cyclin D CDK4". Nature vol. 366: 704–707, Dec. 16, 1993.*

Xiong et al "p21 is a Universal Inhibitor of Cyclin Kinases" Nature vol. 366: 701–704, Dec. 16, 1993.*

Mori et al "Frequent Sematic Mutation of the MTS1/CDK4I Gene in Esophogeal Squamous Cell Carcinoma." Cancer Research vol. 54: 3396–3397, Jul. 1, 1994.*

Hannon et al "p15$^{INK4B}$ is a Potential Effector of TGF–β Induced Cell Cycle Arrest" Nature vol. 371: 257–261, Sep. 15, 1994.*

Hengst et al "A Cell Cycle Regulated Inhibitor of Cyclin–Dependent Kinases" PNAS vol. 91: 5291–5294, Jun. 1994.*

Bartel "Elimination of False Positives That Arise in Using the Two Hybrid System." Biotechniques. vol. 14: 920–924, 1993.*

Fields et al "A Novel Genetic System to Detect Protein–Protein Interactions" Nature vol. 340: 245–246, Jul. 20, 1989.*

Iwabuchi et al "Use of the Two Hybrid System to Identify the Domain of p53 Involves in Oligomerization". Oncogene vol. 8: 1693–1696, 1993.*

* cited by examiner

*Primary Examiner*—Sean McGarry
(74) *Attorney, Agent, or Firm*—Ropes & Gray

(57) ABSTRACT

The present invention relates to the discovery in eukaryotic cells, particularly mammalian cells, of mutant cyclin dependent kinase (CDK) proteins. These proteins fail to bind to CDK-inhibitory proteins and thus lead to aberrant cell growth. Herein, screening assays are described to identify CDK mutant proteins and the uses of these mutant proteins as tumor vaccines is described.

11 Claims, 5 Drawing Sheets

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 1:

TTGAATTCGC CGCCATGGCT ACCTCTCGA                                   29

(2) INFORMATION FOR SEQ ID NO: 2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

AATCTAGAGC CGCCTTGATC CTTTCGGCT                                   29

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CGATATGAGC CAGTGGCTGA AATTGGT                                     27

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

TCCTCCTCCA TTGGGGACTC TCACACT                                     27

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
CGATATGAGC CAGTGGCTGA AATTGGT                                          27
```

(2) INFORMATION FOR SEQ ID NO: 6:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 6:

```
Lys Ala Arg Asp Pro His Ser Gly His Phe Val
 1               5                  10
```

(2) INFORMATION FOR SEQ ID NO: 7:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 7:

```
Lys Ala Cys Asp Pro His Ser Gly His Phe Val
 1               5                  10
```

(2) INFORMATION FOR SEQ ID NO: 8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 8:

```
Ala Cys Asp Pro His Ser Gly His Phe Val
 1               5                  10
```

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

```
Ala Arg Asp Pro His Ser Gly His Phe Val
 1               5                  10
```

CYCLIN DEPENDENT KINASE MUTANTS, AND DIAGNOSTIC AND THERAPEUTIC USES RELATED THERETO

RELATED APPLICATIONS

This application is a continuation-in-part of U.S. Ser. No. 08/581,918 filed Jan. 2, 1996 now U.S. Pat. No. 6,043,030, which is a continuation-in-part of U.S. Ser. No. 08/497,214 filed Jun. 30, 1995 now U.S. Pat. No. 6,331,390, which is a continuation-in-part of U.S. Ser. No. 08/346,147 filed Nov. 29, 1994 which is a continuation-in-part of U.S. Ser. No. 08/306,511 filed Sep. 14, 1994, now U.S. Pat. No. 5,962,316, which is a continuation-in-part of U.S. Ser. No. 08/248,812 filed May 25, 1994, now U.S. Pat. No. 5,889,169, which is a continuation-in-part of U.S. Ser. No. 08/227,371 filed Apr. 14, 1994; which is a continuation-in-part of U.S. Ser. No. 08/154,915 filed Nov. 18, 1993 and now U.S. Pat. No. 6,211,334. The teachings of U.S. Ser. Nos. 08/581,918, 08/497,214 and 08/346,147 (hereinafter the "priority documents") are incorporated herein by reference.

FUNDING

Work described herein was supported by National Institutes under NIH Grant Nos. RO1 GM39620, R01 CA63518, and R01 CA68040 of Health Grant. The United States Government has certain rights in the invention.

BACKGROUND OF THE INVENTION

The cell division cycle is one of the most fundamental processes in biology which, in multicellular organisms, ensures the controlled generation of cells with specialized functions. Under normal growth conditions, cell proliferation is tightly regulated in response to diverse intra-and extracellular signals. This is achieved by a complex network of protooncogenes and tumor-suppresser genes that are components of various signal transduction pathways. Activation of a protooncogene(s) and/or a loss of a tumor suppresser gene(s) can lead to the unregulated activity of the cell cycle machinery. This, in turn, will lead to unregulated cell proliferation and to the accumulation of genetic errors which ultimately will result in the development of cancer (Pardee, $Science$ 246:603–608, 1989).

In the eukaryotic cell cycle a key role is played by the cyclin-dependent kinases (CDKs). CDK complexes are formed via the association of a regulatory cyclin subunit and a catalytic kinase subunit. In mammalian cells, the combination of the kinase subunits (such as cdc2, CDK2, CDK4 or CDK6) with a variety of cyclin subunits (such as cyclin A, B1, B2, D1, D2, D3 or E) results in the assembly of functionally distinct kinase complexes. The coordinated activation of these complexes drives the cells through the cell cycle and ensures the fidelity of the process (Draetta, $Trends\ Biochem.\ Sci.$ 15:378–382, 1990; Sherr, $Cell$ 73:1059–1065, 1993). Each step in the cell cycle is regulated by a distinct and specific cyclin-dependent kinase. For example, complexes of CDK4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the cdc2/cyclin B complex controls the entry into M-phase (Sherr, $Cell$ 73:1059–1065, 1993).

The CDK complex activity is regulated by mechanisms such as stimulatory or inhibitory phosphorylations as well as the synthesis and degradation of the kinase and cyclin subunits themselves. Recently, a link has been established between the regulation of the activity of cyclin-dependent kinases and cancer by the discovery of a group of CDK inhibitors including the $p16^{Ink4a}$, $p15^{Ink4b}$, $p18^{Ink4c}$, $p19/p20^{Ink4d}$, $p21^{Waf1/Cip1}$, $p27^{Kip1}$ and $p57^{kip2}$ proteins. The activity of p21 is regulated transcriptionally by DNA damage through the induction of p53, senescence and quiescence (Harper et al., $Cell$ 75:805–816, 1993). The inhibitory activity of p27 is induced by the negative growth factor TGF-β and by contact inhibition (Polyak et al., $Cell$ 78:66–69, 1994). These proteins, when bound to CDK complexes, inhibit their kinase activity, thereby inhibiting progression through the cell cycle. Although their precise mechanism of action is unknown, it is thought that binding of these inhibitors to the CDK/cyclin complex prevents its activation. Alternatively, these inhibitors may interfere with the interaction of the enzyme with its substrates or its cofactors.

While p21 and p27 inhibit all the CDK/cyclin complexes tested, the Ink4 proteins, e.g., p16, p15, p18 and p19 block exclusively the activity of the CDK4/cyclin D and CDK6/cyclin D complexes in the early G1 phase (Serrano et al., $Nature$ 366:704–707, 1993), by either preventing the interaction of CDK4 and Cyclin D1, or indirectly preventing catalysis. As mentioned above, the p21 is positively regulated by the tumor suppresser p53 which is mutated in approx. 50% of all human cancers. p21 may mediate the tumor suppresser activity of p53 at the level of cyclin-dependent kinase activity. p16 is the product of a tumor suppresser gene localized to the 9p21 locus, which is frequently mutated in human cancer cells.

Of all the various kinases, the CDK4/cyclin D complexes are known to play an important role in regulating cell cycle progression in early G1. These complexes function as integrators of various growth factor-induced extracellular signals and as a link between the different signal transduction pathways and other cyclin-dependent kinases. The expression of the cyclin D1 positive regulatory subunit, is deregulated by gene translocations, retroviral insertions and amplifications in parathyroid adenomas, lymphomas, esophageal and breast carcinomas. The targeted overexpression of cyclin D1 in the mammary epithelium of transgenic mice induces mammary adenomas and adenocarcinomas. This confirms that cyclin D1, when overexpressed, acts as an oncogene (Wang et al., $Nature$ 369:669–671, 1994). Moreover p16 is deleted at high frequency in cell lines derived from tumors of lung, breast, brain, bone, skin, bladder, kidney, ovary, and lymphocyte. These data support the idea that the lack of functional p16 or the overexpression of cyclin D1 leads to the deregulation of CDK4/cyclin D1 kinase activity and thereby contribute to uncontrolled cell proliferation.

SUMMARY OF THE INVENTION

One aspect of the present invention relates to diagnostic assays for determining, in the context of cells isolated from a patient, if mutations have arisen in one or more cyclin dependent kinases of the sample cells. In particular, the assay assesses CDK genes and gene products for mutations that render the a cyclin dependent kinase insensitive to the inhibitory activity of a CKI protein, e.g., an Ink4 protein or a CIP protein. In general, the assay of the instant application detects mutations which alter (e.g., decrease) the association constant (Ka) between a CDK/CKI protein complex. As described herein, the subject assay provides a method for determining if an animal is at risk for a disorder characterized by aberrant cell proliferation, differentiation and/or apoptosis.

Yet another aspect of the present invention relates to the modification of tumor cells, and/or the immune response to tumor cells in a patient by administering a vaccine to enhance the anti-tumor immune response in a host. The present invention provides, for examples, tumor vaccines based on administration of expression vectors encoding a mutant CDK protein, or portion thereof, or immunogenic preparations of polypeptides derived from mutant CDK. In still other embodiments, the tumor vaccine strategy can use the tumor cell itself as a source of tumor antigen.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

DESCRIPTION OF THE DRAWINGS

FIG. 1A: a cDNA library from SK29 melanoma cells in vector pcDNAI/Amp (Invitrogen) was divided in pools of about 200 bacterial colonies. Plasmid DNA from 672 cDNA pools was cotransfected with HLA-A*0201 (inserted with pcDNAI/Amp) into COS-7 cells, and transfectants were screened for antigen expression with CTL3/7. TNF production by CTLs was assessed by measurement of the supernatant cytotxicity to WEHI 164 clone 13 (W13) cells in a colorimetric assay. Each point indicates the screening result with a single cDNA pool. Positive pools, confirmed in an independent experiment, are indicated by their number. As a control, production of TNF by CTLs was measured in the presence of increasing numbers of SK29-MEL-1 cells.$A_{570}$, absorbance at 570 nm.

FIG. 1B: the cDNA clonse C11.1 was cloned from pool 242. Allogeneic melanoma cells were cotransfected with HLA-A*0201 and C11.1 by electroporation and were tested for susceptibility to lysis by CTL anti-C (CTL5/76). Data of a 4-hour, $^{51}$Cr release assay are shown. E/T, effector-to-target ratio. Targets were autologous melanoma cells SK29-MEL-1 (open squares), allogeneic melanoma cells MZ2-MEL-2.2-A2.1 (open circles) cotransfected by eletroporation with HLA-A*0201 and the hygromycin B resistance gene, and MZ2-MEL-2.2-A2.1-C11.1 cells (closed circles) additionally cotransfected with C11.1 and the neomycin resistance gene.

(FIG. 4C) Genomic DNA was extracted from paraffin sections of a lymph node matastasis surgically removed from the patient's left axilla in 1978. A 120-bp CDK4 fragment spanning codons 6 to 43 was amplified with primers 5'-CGATATGAGCCAGTGG CTGA AATTGGT SEQ ID NO:3 and 5'-TCCTCCTCCATTGGGGACTCTCACACT SEQ ID NO:4. No DNA was amplified when PCR was performed withprimers5'-CGATATGAGCCAGTGGCTGAAATTGGT SEQ ID NO:5 (sense) and Sp6 (antisense) under conditions that allowed detection of 0.04 pg of C11.1 DNA, thus excluding contamination from the C11.1 plasmid. PCR fragments were purified with the QIAquick PCR purification kit (Qiagen) and directly sequenced with an automated sequencing devisce (Applied Biosystems AB1373A).

Bottom panels: closed circles, ACDPHSGHFV SEQ ID NO:8, open circles, ARDPHSGHFV SEQ ID NO:9, changes in the residues are underlined. (Abbreviations for the amino acid residues are: A, Ala;; C, Cys; D, Asp; F, Phe; G, Gly; H, His; K, Lys; P, Pro; R, Arg; S, Ser; and V, Val.) The data are the means of duplicate samples from one experiment and were confirmed in six independent experiments. Peptides were synthesized by a standard solid-phase method with a ,ultiplepeptide synthesizer (Abimed 422). The purity of the peptides was determined by analytical reversed-phase high-performance liquid chromatography and proved to be at least 80% pure (UV, 214 nm). Their integrity was determined on a Lasermat mass spectrometer (Finnigan MAT).

Figure 5A:
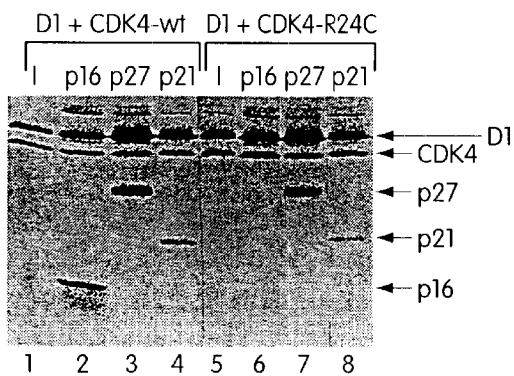
Figure 5B:
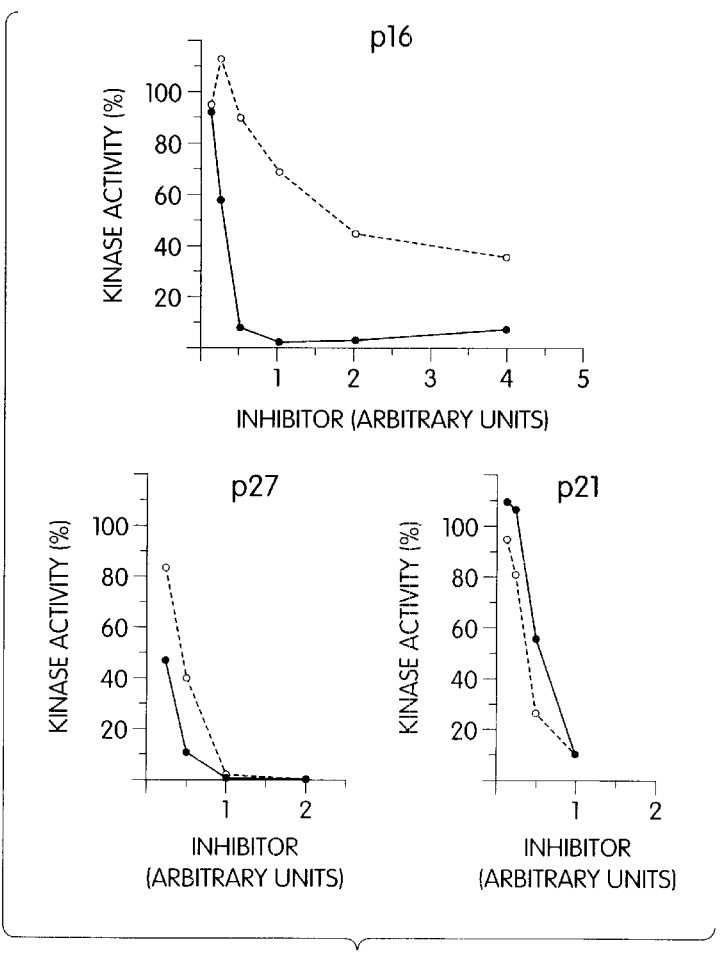

FIGS. 5A and 5B illustrate the impaired interaction of CDK4-R24C with $p16^{INK4a}$.

FIG. 5A: Immunoprecipitation with CDK4 antibodies of $^{35}$S-labeled insect cell extracts (2 $\mu$l) containing CDK4-wt and cyclin D1 (lanes 1 to 4), or CDK4-R24 and cyclin D1 (lanes 5 to 8) mixed with similar extracts (2 $\mu$l) containing p16 (lanes 2 and 6), p27 (lanes 3 and 7), or p21 (lanes 4 and 8). Immunoprecipitations were performed in a final volume of 40 $\mu$l.

FIG. 5B: Kinase assays of insect cell extracts (2 $\mu$l) containing CDK4-wt and cyclin D1 (closed circles) or CDK4-R24C and cyclin D1 (open circles) mixed with increasing amounts (twofold increments) of extracts containing p16, p27, and p21. Final mixtures (10 $\mu$l) were assayed for their ability to phosphorylate glutathione-S-transferase fused to an Rb deletion fragment containing residues 373 to 928 (Rb large pocket). The total amount of insect cell extract in each mixture was compensated for by addition of a simliar extract containing the baculoviral polyhedrin protein. The amount of the different inhibitors is expressed in arbitrary units: one unit corresponds to 1 $\mu$l of p16 extract, 0.5 $\mu$l of p27 extract, and 4 $\mu$l of p21 extract. Quantification was done in a Fuji Phosphoprimager, and percentages refer to the activity in the absence of added inhibitors. The absolute activities of CDK4-wt and cyclin D1 and CDK4-R24C and cyclin D1 in the absence of added inhibitors was similar.

DETAILED DESCRIPTION OF THE INVENTION

Progression through the cell-cycle is marked by a series of irreversible transitions that separate discrete tasks necessary for faithful cell duplication. These transitions are negatively regulated by signals that constrain the cell-cycle until specific conditions are fulfilled. Entry in to mitosis, for example, is inhibited by incompletely replicated DNA or DNA damage. These restrictions on cell-cycle progression are essential for preserving the fidelity of the genetic information during cell division. The transition from $G_1$ to S phase, on the other hand, coordinates cell proliferation with environmental cues, after which the checks on the cell-cycle progression tend to be cell autonomous. Among the signals that restrict cell-cycle progression during $G_1$ are extracellular proteins which inhibit cell proliferation, growth factor or amino acid depletion, and cell-cell contact. Disruption of these signaling pathways uncouples cellular responses from environmental controls and may lead to unrestrained cell proliferation.

Eukaryotic cells, in general, require cyclin-dependent kinases (CDKs) for progression through $G_1$ and entry into S phase. In mammalian cells, both D-and E-type cyclins are rate limiting for the $G_1$ to S transition, and both reduce, but do not eliminate, the cell's requirement for mitogenic growth factors. Recently cyclins and CDKs have been found to be negatively regulated by either intracellular or extracellular signals that inhibit cell proliferation.

A family of related cell-cycle regulatory proteins, termed "Ink4 proteins" (previously "CCR proteins", see priority documents) typically function to restrict progression of a cell through mitosis, and are likely to be involved in controlling progression through meiosis. Members of this family, apparently evolutionarily related, can be generally characterized by (i) a polypeptide sequence giving rise to a series of ankyrin-like repeats, and (ii) the ability to bind to a cyclin dependent kinase. The Ink4 protein family includes the p15, p16, p18, p19/p20 proteins. These proteins, when bound to CDK complexes, inhibit their kinase activity, thereby inhibiting progression through the cell cycle. Moreover, data from hybridization and immunoprecipitation experiments indicates still other members of the Ink4 family exist, comprising proteins representing both evolutionarily divergent sequences as well as differentially spliced variants.

One function of members of this family of proteins in cell-cycle regulation is in modulating the activity of cyclin/CDK complexes during various stages of the cell-cycle, particularly those which include CDKs active in progession through the $G_1$ phase, such as CDK4 or CDK6. To illustrate, both p16 and p15 are demonstrated in the priority documents to exert an inhibitory effect on the activity of cyclin/CDK complexes, particularly those which include CDK4 or CDK6. For instance, each protein is able to inhibit the activity of cyclin D1/CDK complexes in vivo. Moreover, the diversity of members of the Ink4 protein family, like the diversity of CDKs, is suggestive of individualistic roles of each member of this family, which may be tissue-type or cell-type specific, occur at different points in the cell-cycle, occur as part of different extracellular or intracellular signaling pathways, or a combination thereof.

Previously, certain of the Ink4 proteins have been shown to be deleted or mutated at high frequency in tumors, such as derived from lung, breast, brain, bone, skin, bladder, kidney, ovary, or lymphocytes. In addition to mutant forms of Ink4 proteins which have been identified, the present invention discloses mutant forms of CDK proteins which fail to bind to Ink4 proteins. Thus, from our in vitro and in vivo observations concerning such CDK mutants, it is understood that mutations which render a cyclin dependent kinase insensitive to an Ink4 protein have the ability to transform cells and, as described in the appended examples, have been identified as a phenotype for certain cancer cells.

On aspect of the instant invention is based on the discovery that mutations, in addition to those causing overexpression, to such CDKs as CDK4 or CDK6 (e.g., $G_1$ phase CDKs) apparently functionally mimic the loss of Ink4 gene(s) performance, and are useful diagnostic markers for risk assessment and phenotyping cell and tissue samples. Accordingly, the present invention makes available diagnostic assays and reagents for detecting such mutations to CDK proteins in order to aid in the diagnosis and phenotyping of proliferative disorders arising from, for example, tumorigenic transformation of cells, or other hyperplastic or neoplastic transformation processes, as well as differentiative disorders, such as degeneration of tissue, e.g. neurodegeneration. For example, the present invention makes available screening assays for detecting alterations in the formation of Ink4/CDK complexes, and/or mutations to CDK proteins which give rise to loss of senstivity to inhibitoriy activities of one or more Ink4 proteins.

By the present method, there is provided a method for evaluating an individual's risk (e.g., likelihood) of having or developing a disorder marked by abberant proliferation or dedifferentiation. Where such disorders have already been diagnosed, the present method, by facilitating careful phenotyping of transformed cells, can improve the choice of intervention strategies by clinicians. For instance, the choice of an anit-proliferitive agent may be influenced by the knowledge of whether loss of regulation of CDK4 and/or CDK6 occurs through loss of an Ink4 gene product, e.g., such that Ink4 gene replacement is a therapeutic option, or occurs through mutations to the CDK which render it insenstive to an Ink4 protein, in which case Ink4 gene replacement is not a desirable option.

Moreover, from the paradigm which develops from observing such mutations to the CDK proteins relative to the Ink4 proteins, another aspect of the present invention relates to diagnostic assays and reagents for detecting mutations to cyclin dependent kinases which result in loss of CIP protein (defined below) regulation of the kinases. Thus, another aspect of the present invention concerns an assay for detecting mutations to cyclin dependent kinases which reduce the binding of such CIP proteins as $p21^{CIP1}$, $p27^{KIP1}$, and $p57^{KIP}2$.

Still other aspects of the present invention, as described in further detail below, relate to various uses for the mutant CDK proteins, e.g. ranging from transforming reagents to tumor vaccines.

I. Definitions

For convenience, certain terms employed in the specification, examples, and appended claims are collected here.

An "inhibitor of CDK activation" refers to a molecule able to interact with a cyclin dependent kinase and prevent activation of a kinase activity of the CDK either by, for example, inhibiting formation of CDK complexes including regulatory subunits, inhibiting interaction of the CDK subunit with activating kinases or phosphatases, inhibiting substrate binding, inhibiting ATP binding, and/or inhibiting conformational changes required for enzymatic activity. Accordingly, such inhibition may be by a direct, competitive mechanism, or by an indirect, non- or uncompetitive mechanism.

To this end, the term "CKI protein" refers to a protein which is an inhibitor of CDK activation. Exemplary CKI proteins include members of the Ink4 family, such as $p16^{Ink4A}$ or $p15^{Ink4B}$, and members of the CIP family, such as $p21^{CIP1}$, $p27^{KIP1}$, and $p57^{KIP2}$.

The term "Ink4 protein" refers to a family of structurally related CDK inhibitors characterized by a fourfold repeated ankyrin-like sequence (Elledge et al. (1994) Curr. Opin. Cell Biol. 6:874–878), and the ability to bind to CDKs, especially CDK4 and CDK6. Exemplary members of this protein family include p16 (Ink4A/MTSI; Serrano et al (1993) Nature 366:704–707); p15 (Ink4B; Hannon et al. (1994) Nature 371:257–261); p18 (Ink4c; Guan et al. (1994) Genes Dev. 8:2939–2952) and p19/p20 (Ink4d; Chan et al. (1995) Mol. Cell Biol. 15:2682–2688; and Hirai et al. (1995) Mol. Cell Biol. 15:2672–2681). A wild-type p16 protein, for example, binds CDK4 with approximately (e.g., within about 20%) the same association constant as the p16 protein described by Serrano et al., supra).

The term "CIP protein" refers to members of another CKI protein family which includes $p21^{CIP1}$ (WAF1/SDI1/CAP20; Xiong et al. (1993) Nature 366:701–704); $p27^{KIP1}$ (Polyak et al. (1994) Cell 78:67–74); and $p57^{KIP2}$ (Lee et al. (1995) Genes Dev. 9:639–649; and Matsuoka et al. (1995) Genes Dev. 9:650–662). In addition to the functional characteristic of CDK inhibition, the CIP proteins each have a CDK inhibitory motif (a CDK-binding motif) of about 50 amino acids, referred to herein as a "p21/p27" inhibitory domain, which is conserved in members of the CIP family. A wild-type p21 protein, for example, binds CDK with approximately (e.g., within about 20%) the same association constant as the p21 protein described by Xiong et al., supra).

The terms "CKI-insenstive CDK" protein and the "subject mutant CDK" protein, which are used interchangeably herein, refer to a cyclin dependent kinase protein which is mutated at one or more amino acid positions, e.g., by insertion, deletion or change in amino acid composition, such that the mutated CDK protein has a diminished capacity, relative to the wild-type form of the protein, to bind to a CKI protein such as an Ink4 protein or a CIP protein.

A "cyclin dependent kinase" or "CDK" are art recognized terms referring to protein of the family of proteins which include catalytic subunits of cyclin/CDK complexes. Exemplary CDK proteins include CDC2, CDK2, CDK3, CDK4, CDK5, CDK6 and CDK7. The sequence for wild-type CDK protein can be found, in GenBank.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding a cell-cycle regulator of the present invention, including both exon and (optionally) intron sequences. In preferred embodiments, the nucleic acid is DNA or RNA. The term "intron" refers to a DNA sequence present in a given Ink4 gene which is not translated into protein and is generally found between exons.

The terms protein, polypeptide, and peptide are used interchangably herein.

The phrase "aberrant modification or mutation" of a gene refers to such genetic lesions as, for example, deletion, substitution or addition of nucleotides to a gene, as well as non-wild type splicing of mRNA transcribed from the gene. Mis-expression of a gene, on the other hand, refers to aberrant levels of transcription of the gene relative to those levels in a normal cell under similar conditions.

The term "transfection" refers to the introduction of a nucleic acid, e.g., an expression vector, into a recipient cell by nucleic acid-mediated gene transfer. "Transformation", as used herein respecting transfected nucleic acid, refers to a process in which a cell's genotype is changed as a result of the cellular uptake of exogenous DNA or RNA, and, for example, the transformed cell expresses a recombinant form of one of the subject mutant CDK proteins, e.g. CDK4 or CDK6.

"Cells" or "cell cultures" or "recombinant host cells" or "host cells" are often used interchangeably as will be clear from the context. These terms include the immediate subject cell which expresses the mutant CDK protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant CDK protein.

As used herein, the term "vector" refers to a nucleic acid molecule capable of transporting another nucleic acid to which it has been linked. The term "expression vector" includes plasmids, cosmids or phages capable of synthesizing the subject CDK protein encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a fusion protein of the present invention) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes The ability to replicate in a host, usually conferred by an origin of replication, and a selection gene to facilitate recognition of transformants may additionally be incorporated. Vectors derived from viruses, such as retroviruses, adenoviruses, and the like, may be employed.

"Operably linked" when describing the relationship between two DNA regions simply means that they are functionally related to each other. For example, a promoter or other transcriptional regulatory sequence is operably linked to a coding sequence if it controls the transcription of the coding sequence.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant CDK gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a neuronal lineage, e.g. glial cells, or alternatively, in epithelial cells, e.g. melanocytes. In an illustrative embodiment, gene constructs utilizing glial-specific promoters can be used as a part of gene therapy to cause expression of recombinant forms of one of the subject CDK proteins in glioma cells with a feature of the gene construct being a tissue-specific promoter for directing expression of the subject protein in only glial tissue. The term also covers so-called "leaky" promoters, which regulate expression of a selected DNA primarily in one tissue, but cause expression in other tissues as well.

As used herein, a "reporter gene construct" is a nucleic acid that includes a "reporter gene" operatively linked to a transcriptional regulatory sequences. Transcription of the reporter gene is controlled by these sequences. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences are recognized by effector molecules.

The term "aberrant proliferation" refers to proliferation of cells which is undesired, e.g., such as may arise it due to transformation and/or immortalization of the cells, e.g., neoplastic or hyperplastic, for purposes of wound healing, cosemetic, etc.

The term "aberrant dedifferentiation" refers to loss of differentiation of cells of a tissue such that the afflicted tissue losses at least a portion of the normal phenotype and function for animal at that development stage. For example, adult tissue undergoing aberrant dedifferentiation will be characterized by loss of at least a portion of the functional perfomance of that tissue in an adult organism.

The term "aberrant apoptosis" refers to unwanted cell death caused by apoptosis, e.g., as may occur in a variety of degenerative disorders, including such neurodegenerative disorders as Alzheimer's disease and Parkinson's disease.

An "immunological response" to a immunogen or tumor vaccine is the development in the host of a cellular and/or antibody-mediated immune response to the composition or vaccine of interest. Usually, such a response consists of the subject producing one or more of antibodies, B cells, helper T cells, suppressor T cells, and/or cytotoxic T cells directed specifically to an antigen or antigens included in the composition or vaccine of interest.

The term "patient" refers to an animal, preferably a mammal, including humans as well as livestock and other veterinary subjects.

II. Diagnostic Assays

As set out above, one aspect of the present invention relates to diagnostic assays for determining, in the context of cells isolated from a patient, if mutations have arisen in one or more cyclin dependent kinases of the sample cells. In particular, the assay assesses CDK genes and gene products for mutations that render the a cyclin dependent kinase insensitive to the inhibitory activity of a CKI protein, e.g., an Ink4 protein or a CIP protein. In general, the assay of the instant application detects mutations which alter (e.g., decrease) the association constant (Ka) between a CDK/CKI protein complex. As described herein, the subject assay provides a method for determining if an animal is at risk for a disorder characterized by aberrant cell proliferation, differentiation and/or apoptosis. In preferred embodiments, the method can be generally characterized as including a step of detecting, in a sample of cells from the subject, the presence or absence of a genetic lesion characterized by an alteration to a CDK gene, such as CDK4 or CDK6 genes, ultimately affecting the ability of the CDK gene product to bind to one or more CKI proteins. To illustrate, such genetic lesions can be detected by ascertaining the existence of at least one of (i) a deletion of one or more nucleotides from a CDK gene, (ii) an addition of one or more nucleotides to a CDK gene, (iii) a substitution of one or more nucleotides of a CDK gene, and (iv) the presence of a non-wild type splicing pattern of a messenger RNA transcript of a CDK gene. As set out below, the present invention provides a large number of assay techniques for detecting lesions in cyclin dependent kinase genes, and importantly, provides the ability to discern between different molecular causes underlying CDK-dependent aberrant cell growth, proliferation and/or differentiation.

In certain embodiments, detection of the lesion comprises utilizing a nucleic acid probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in a sample CDK gene (see Abravaya et al. (1995) *Nuc Acid Res* 23:675–682). In a merely illustrative embodiment, the method includes the steps of: (i) collecting a sample of cells from a patient; (ii) isolating nucleic acid (e.g., genomic, mRNA) from the cells of the sample; (iii) contacting the nucleic acid sample with one or more primers which specifically hybridize to a CDK gene under conditions wherein hybridization and amplification of the CDK gene (if present) occurs, and (iv) detecting, by virtue of the presence or absence of the amplification product, the size of the amplification product, the sequence of the amplification product and/or a restriction map of the amplification product (e.g., compared to a control sample) whether a mutation exists in the sample CDK gene. Alternatively, PCR and/or LCR may be used as preliminary amplification steps in conjunction with any of a variety of other techniques used for detecting mutations, such as described herein.

In a preferred embodiment of the subject assay, mutations in a CDK gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Mutations in CDK4 have been identified using such methods. For instance, as described in the appended examples, the mutation of Arg to Cys at amino acid position 24 can results in creation of a HindIII site in the mutated gene. Thus, restriction fragment length polymorphisms with HindIII or other restriction enzymes, either created or lost relative to the wild-type CDK coding sequence, can be used to detect CDK mutations which may give rise to loss of CKI binding. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the CDK gene and detect mutations by comparing the sequence of the sample CDK with the corresponding wild-type (control) sequence. Exemplary sequencing reactions include those based on techniques developed by Maxim and Gilbert (Maxim et al. (1977) *PNAS* 74:560) or Sanger (Sanger et al. (1977) *PNAS* 74:5463). It is also contemplated that any of a variety of automated sequencing procedures may be utilized when performing the subject assays (Biotechniques (1995) 19:448), including by sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). Moreover, for large scale sequencing, e.g., of many patient samples, art recognized multiplexing and/or deconvolution techniques can be adpated to the sequencing of CDK genes. It will be evident to one skilled in the art that, for certain embodiments, the occurence of only one, two or three of the nucleic acid bases need be determined in the sequencing reaction. For instance, A-tract sequencing or the like, e.g., where only one nucleic acid is detected, can be carried out.

In a further embodiment, protection from cleavage agents (such as a nuclease, hydroxylamine or osmium tetroxide and with piperidine) can be used to identify fine mutations in a CDK gene by detecting mismatched bases in RNA/RNA or RNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type CDK sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *PNAS* 85:4397; Saleeba et al (1992) *Methods Enzymod* 217:286–295. In a preferred embodiment, the control DNA or RNA can be labeled for detection.

In still another embodiment, the mismatch cleavage reaction for detecting and mapping point mutations in CDK cDNAs can employ one or more proteins that recognize mismatched base pairs in double-stranded DNA (so called "DNA mismatch repair" enzymes). For example, the mutY enzyme of *E. coli* cleaves A at G/A mismatches and the thymidine DNA glycoslase from HeLa cells cleaves T at G/T mismatches (Hsu et al. (1994) *Carcinogenesis* 15:1657–1662). According to an exemplary embodiment, a probe based on a CDK sequence, e.g., a wild-type CDK sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CDK genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control CDK nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which a known mutation, such as the C→T mutation described below, is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In still another embodiment, mutations to a CDK protein can be detected by immunoassay. Antibodies which are selectively immunoreactive with a mutant form of a cyclin dependent kinase, relative to the wild-type protein can be generated by such methods as described below. In an illustrate method, the cells of a biopsy sample can be lysed and (optionally) chromatographed, or made permeable to antibody, and the level of expression of a mutant CDK can be detected by standard immunoassay techniques such mutant-specific antibodies.

In yet another embodiment, a diagnostic assay is provided which detects the ability of a CDK gene product, e.g., isolated from a biopsied cell, to bind to a CKI protein. For instance, as set out above, one goal of the subject assay is to detect CDK4 and/or CDK6 mutants which, while expressed at normal levels in a sample of cells, are defective at binding an Ink4 protein(s). It will be understood that mutations to a CDK sequence may arise from fine mutations, e.g., point mutants, which may be impractical to detect by the diagnostic DNA sequencing techniques or by the immunoassays described because they have not previously characterized. The present invention accordingly further contemplates diagnostic screening assays which generally comprise cloning one or more CDK genes from the sample cells, and expressing the cloned genes under conditions which permit detection of an interaction between that recombinant gene product and a target protein, e.g., a CKI such as an Ink4 protein or a CIP protein.

A wide variety of techniques can be used to determine the ability of a CDK protein to bind to other proteins. These techniques can be used to detect mutations in a CDK gene which give rise to mutant CDK proteins with a higher or lower binding affinity for a CKI protein relative to the wild-type cyclin dependent kinase.

In an exemplary embodiment, a CDK transcript is amplified from cells of a patient sample, e.g., by PCR, cloned into an expression vector, and transformed into an appropriate host cell. In an exemplary screening assay of the present invention, the sample CDK protein is contacted with an isolated and purified CKI polypeptide, which is ordinarily capable of binding CDK4. The complex formation of the sample CDK protein and the CKI polypeptide can be measured directly, or the ability of the sample CDK protein to inhibit complex formation of a labelled, wild-type CDK polypetede with the CKI polypeptide may be assessed. In the control assay, an isolated and purified wild type CDK protein is added in place of the sample CDK.

In other embodiments, the ability of a CKI protein to isolate a CDK protein from a cell lysate can be used to detect mutations to a CDK protein which reduce its ability to bind to the CKI bait protein.

Complex formation between the CKI and CDK polypeptides may be detected by a variety of techniques. For instance, formation of complexes can be quantitated using, for example, detectably labelled proteins such as radiolabelled (e.g. $^{32}P$, $^{35}S$, $^{14}C$ or $^{3}H$), fluorescently labelled (e.g. FITC), or enzymatically labelled CKI or CDK polypeptides, by immunoassay, or by chromatographic detection. The use of an enzymatically labeled CDK protein will, of course, generally be used only when enzymatically inactive portions of the CDK are used, as this protein can possess a measurable intrinsic activity that can be detected.

Typically, it will be desirable to immobilize either the CKI polypeptide or the CDK polypeptide to facilitate separation of CKI/CDK complexes from uncomplexed forms of one or both of the proteins, as well as to accommodate automation of the assay. Binding of the CDK and CKI polypeptides can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. To illustrate, glutathione-S-transferase/p16 (GST/p16) fusion proteins can be adsorbed onto glutathione sepharose beads (Sigma Chemical, St. Louis, Mo.) or glutathione derivatized microtitre plates, which are then combined with a sample CDK4 polypeptide, e.g. from a cloned gene or from a cell lysate, and the mixture incubated under conditions conducive to complex formation, e.g. at physiological conditions for salt and pH. Following incubation, the beads are washed to remove any unbound CDK4 polypeptide, and the matrix immobilized CDK polypeptide determined directly (e.g. by immunoassay), or in the supernatant after the p16/CDK4 complexes are subsequently dissociated. Alternatively, the complexes can dissociated from the matrix, separated by SDS-PAGE, and the level of CDK4 polypeptide found in the immobilized fraction quantitated from the gel using standard electrophoretic techniques such as described in the appended examples.

Other techniques for immobilizing proteins on matrices are also available for use in the subject assay. For instance, either of the CKI or CDK polypeptides can be immobilized utilizing conjugation of biotin and streptavidin. For example, biotinylated p16 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the p16 (or a heterologous epitope added thereto) but which do not interfere with CDK4 binding can be derivatized to the wells of the plate, and the p16 trapped in the wells by antibody conjugation. As above, preparations of a CDK4 polypeptide from a cell sample is incubated in the p16-presenting wells of the plate, and the amount of p16/CDK4 complex trapped in the well is quantitated. Exemplary methods for detecting such complexes, in addition to those described above for the GST-immobilized complexes, include immunodetection of complexes using antibodies reactive with the CDK4 polypeptide, or which are reactive with the p16 protein and compete for binding with the CDK4 polypeptide; as well as enzyme-linked assays which rely on detecting an enzymatic activity associated with the CDK4 polypeptide, either intrinsic or extrinsic activity. In the instance of the latter, the enzyme can be chemically conjugated or provided as a fusion protein with a CDK4 polypeptide. To illustrate, the CDK4 polypeptide can be chemically cross-linked or genetically fused with horseradish peroxidase, and the amount of CDK4 polypeptide trapped in the complex can be assessed with a chromogenic substrate of the enzyme, e.g. 3,3'-diaminobenzadine terahydrochloride or 4-chloro-1-napthol. Likewise, a fusion protein comprising the CDK4 polypeptide and glutathione-S-transferase can be provided, and complex formation quantitated by detecting the GST activity using 1-chloro-2,4-dinitrobenzene (Habig et al (1974) J Biol Chem 249:7130). Direct detection of the kinase activity (intrinsic) of CDK4 can be provided using substrates known in the art, e.g., histone HI or Rb.

For processes which rely on immunodetection for quantitating one of the proteins trapped in the complex, antibodies against the protein, such as either anti-CDK or anti-CKI antibodies, can be used. Alternatively, the protein to be detected in the complex can be "epitope tagged" in the form of a fusion protein which includes, in addition to the CDK or CKI polypeptide sequence, a second (heterologous) polypeptide portion for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In yet another embodiment of the subject screening assay, a two hybrid assay (also called the "interaction trap assay" or "ITS"), can be used to detect mutations in a CDK gene which alter complex formation with CKI proteins. Accordingly, the present invention provides a convenient method for detecting mutants of CDK genes encoding proteins which are unable to physically interact with a CKI "bait" protein by detecting the reconstitution of a transcriptional activator in a CKI/CDK-dependent fashion. Exemplary ITS systems which can be exploited to generate the subject assay are described in, for example, U.S. Pat. No. 5,283,317; PCT publication WO94/10300; Zervos et al. (1993) Cell 72:223–232; Madura et al. (1993) J Biol Chem 268:12046–12054; Bartel et al. (1993) Biotechniques 14:920–924; and Iwabuchi et al. (1993) Oncogene 8:1693–1696.

In particular, the method makes use of chimeric genes which express hybrid proteins. To illustrate, a first hybrid gene comprises the coding sequence for a DNA-binding domain of a transcriptional activator fused in frame to the coding sequence for a bait protein, e.g., a CKI polypeptide which is capable of binding a wild-type CDK protein. The second hybrid protein encodes a transcriptional activation domain fused in frame to a gene encoding the sample protein, e.g. a CDK, such as cDNA amplified from a cell sample of a patient. If the bait and sample proteins are able to interact, e.g., form a CDK/CKI complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the bait and sample proteins. As will be appreciated, the DNA-binding and transcriptional activation domains can be swapped between the CDK and CKI fusion proteins. The point is merely to provide the two domains on separate proteins such that reconstitution of a functional activator is mediated by the other heterologous components of the fusion proteins.

In accordance with the present invention, the method includes providing a host cell, preferably a yeast cell, most preferably Saccharomyces cerevisiae or Schizosaccharomyces pombe. The host cell contains a reporter gene having a binding site for the DNA-binding domain of a transcriptional activator, such that the reporter gene expresses a detectable gene product when the gene is transcriptionally activated. Such activation occurs when the activation domain of the transcriptional activator is brought into sufficient proximity to the DNA-binding domain of a transcriptional activator bound to the regulatory element of the reporter gene. The first chimeric gene may be present in a chromosome of the host cell, or as part of an expression vector.

A first chimeric gene is provided which is capable of being expressed in the host cell. The gene encodes a chimeric "bait" protein which comprises (i) a DNA-binding domain that recognizes the responsive element on the reporter gene in the host cell, and (ii) a CKI polypeptide sequence, e.g., an Ink4 protein or a CIP protein, which is capable of binding to a wild-type CDK protein.

A second chimeric gene is provided which is capable of being expressed in the host cell. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid. The second chimeric gene includes a DNA sequence that encodes a second hybrid protein comprising a transcriptional activation domain fused to the sample CDK protein, or a fragment thereof, which is to be tested for interaction with the bait CKI protein. In an exemplary embodiment, the nucleic acid encoding the "fish" protein includes, as the CDK polypeptide portion, a sequence which is cloned from the cells of a patient sample.

Preferably, the DNA-binding domain of the first hybrid protein and the transcriptional activation domain of the second hybrid protein are derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moeity contains no activation function and has no known effect on transcription of yeast genes. In addition, use of LexA allows control over the sensitivity of the assay to the level of interaction (see, for example, the Brent et al. PCT publication WO94/10300).

The CDK/CKI mediated interaction, if any, between the bait and fish fusion proteins in the host cell, therefore, causes the activation domain to activate transcription of the reporter gene. The method is carried out by introducing the first chimeric gene and the second chimeric gene into the host cell, and subjecting that cell to conditions under which the first hybrid protein and the second hybrid protein are expressed in sufficient quantity for the reporter gene to be activated. The formation of a CDK/CKI complex results in a detectable signal produced by the expression of the reporter gene. Accordingly, the formation of a complex between a sample CDK protein and a CKI protein can be compared to a wild-type CDK/CKI complex by evaluating the level of expression of the reporter gene for two hybrids derived with each.

In an illustrative embodiment, *Saccharomyces cerevisiae* YPB2 cells are transformed simultaneously with a plasmid encoding a GAL4db-Ink4 fusion and with a plasmid encoding the GAL4ad domain fused to a a CDK gene which has been PCR amplified from a cell sample. Moreover, the strain is transformed such that the GAL4-responsive promoter drives expression of a phenotypic marker. For example, the ability to grow in the absence of histidine can depends on the expression of the LacZ gene. When the LacZ gene is placed under the control of a GAL4-responsive promoter, the yeast cell will turn blue in the presence of β-gal if a functional GAL4 activator has been reconstituted through the interaction of Ink4 and the sample CDK proteins. Thus, a convenient readout method is provided. Other reporter constructs will be apparent, and include, for example, reporter genes which produce such detectable signals as selected from the group consisting of an enzymatic signal, a fluorescent signal, a phosphorescent signal and drug resistance.

A similar method modifies the interaction trap system by providing a "relay gene" which is regulated by the transcriptional complex formed by the interacting bait and fish proteins. The gene product of the relay gene, in turn, regulates expression of a reporter gene, the expression of the latter being what is scored in the modified ITS assay. Fundamentally, the relay gene can be seen as a signal inverter.

As set out above, in the standard ITS, interaction of the fish and bait fusion proteins results in expression of a reporter gene. However, where mutations to the sample CDK protein are to be detected, a positive readout from the reporter gene of the presence of such mutations requires detecting inhibition (or lack of expression) of the reporter gene.

In an inverted ITS system, the fish and bait proteins positively regulate expression of the relay gene. The relay gene product is in turn a repressor of expression of the reporter gene. Inhibition of expression of the relay gene product by inhibiting the interaction of the fish and bait proteins results in concomitant relief of the inhibition of the reporter gene, e.g., the reporter gene is expressed. For example, the relay gene can be the repressor gene under control of a promoter sensitive to the fish and bait fusion proteins described above. The reporter gene can accordingly be a positive signal, such as providing for growth (e.g., drug selection or auxotrophic relief), and is under the control of a promoter which is constitutively active, but can be suppressed by the repressor protein (the relay gene product). In the absence of a mutation to the sample CDK which inhibits the interaction of the fish and bait protein, the repressor protein is expressed. In turn, that protein represses expression of the reporter gene. However, a mutation to the sample CDK protein which disrupts binding to the CKI polypeptide forming the bait protein results in a decrease in repressor expression, and consequently an increase in expression of the reporter gene as repression is relieved. Hence, the signal is inverted.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not.

In the case of yeast, suitable positively selectable (beneficial) genes include the following: URA3, LYS2, HIS3, LEU2, TRP1; ADE1,2,3,4,5,7,8; ARGl, 3, 4, 5, 6, 8, HIS1, 4, 5; ILV1, 2, 5; THR1, 4; TRP2, 3, 4, 5, LEU1, 4; MET2,3,4,8,9,14,16,19; URA1,2,4,5,10; H0M3,6; ASP3; CHO1; ARO 2,7; CYS3; OLE1; IN0,1,2,4; PR01,3. Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation of the gene leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

The marker gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exbl gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment.

The interactive trap system, as described above, may be practiced using a kit for detecting interaction between a target protein and a sample protein. In an illustrative embodiment, the kit includes a container, two vectors, a host cell, and (optionally) a set of primers for cloning one or more CDK proteins from a patient sample. The first vector contains a promoter and may include a transcription termination signal functionally associated with the first chimeric gene in order to direct the transcription of the first chimeric gene. The first chimeric gene includes a DNA sequence that encodes a DNA-binding domain and a (unique) restriction site(s) for inserting a DNA sequence encoding the target protein or protein fragment in such a manner that the target protein is expressed as part of a hybrid protein with the DNA-binding domain. The first vector also includes a means for replicating itself (e.g., an origin of replication) in the host cell and (optionally) in bacteria. In preferred embodiments, the first vector also includes a first marker gene, the expression of which in the host cell permits selection of cells containing the first marker gene from cells that do not contain the first marker gene. Preferably, the first vector is a plasmid.

The kit also includes a second vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the sample protein, or fragment thereof, into the vector in such a manner that the target protein is capable of being expressed as part of a hybrid protein with the transcriptional activation domain.

The second vector may further include a means for replicating itself in the host cell and in bacteria. The second vector can also include a second marker gene, the expression of which in the host cell permits selection of cells containing the second marker gene from cells that do not contain the second marker gene.

In general, the kit will also be provided with one of the two vectors already including the bait protein. For example, the kit can be configured for detecting mutations to a CDK gene which result in loss of binding to CCR. Accordingly, the first vector could be provided with a CKI open reading frame fused in frame to the DNA-binding domain to provide a CKI bait protein. Open reading frames for a CDK protein can be cloned from a cell sample and ligated into the second vector in frame with the activation domain.

Where the kit also provides primers for cloning a CDK gene into the two hybrid assay vectors, the primers will preferably include restriction endonuclease sites for facilitating ligation of the amplified gene into the insertion site flanking the DNA-binding domain or activating domain.

In an exemplary embodiment, the primers are chosen to specifically amplify one CDK gene. For example, primers based on unique CDK4 coding sequence can be used to amplify and subclone CDK4 mRNA into a vector of the subject assay. Likewise, primers specific for a CDK6 gene, can be used to subclone a CDK6 message from a cell sample and the ability of these gene products to interact with a CKI protein, e.g., an Ink4 protein, can be determined.

The kit includes a host cell, preferably a yeast strain of *Saccharomyces cerevisiae* or *Schizosaccharomyces pombe*.

The host cell contains the reporter gene under the transcriptional control of a responsive element for the DNA-binding domain of the first hybrid protein, e.g., the resonsive element is positioned so that the reporter gene expresses a detectable product when the gene is activated by the transcriptional activation domain encoded by the second vector. The host cell, by itself, is incapable of expressing a protein having a function of the first marker gene, the second marker gene, the DNA-binding domain, or the transcriptional activation domain.

III. Nucleic Acids, Proteins and Antibodies

Yet another aspect of the present invention pertains to isolated nucleic acids comprising nucleotide sequences encoding mutant CDK polypeptides, e.g., CDK proteins which retain their kinase activity and ability to bind cyclins, but which have lost the ability to bind to one or more CKI proteins. Exemplary CDK polypeptides are characterized by diminished association constants ($K_a$), relative to the wild-type enzyme subunit (e.g., as found in GenBank), for one or more CKI proteins. In preferred embodiments, the mutant CDK protein is characterized by a $K_a$ for binding to a CKI protein at least one order of magnitude less than the corresponding wild-type CDK protein, and more preferably at least two, three, four or five orders of magnitude less. Preferred CDK polypeptide of the present invention are derived from CDC2, CDK2, CDK3, CDK4 or CDK6, most preferably from CDKs which bind Ink4 proteins, such as CDK4 and CDK6.

The present invention also provides expression vectors containing a nucleic acid encoding an CKI-insensitive CDK polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject CDK proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990).

For instance, any of a wide variety of expression control sequences, sequences that control the expression of a DNA sequence when operatively linked to it, may be used in these vectors to express DNA sequences encoding CDK polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

The subject expression vectors can be used to transfect cells and thereby produce polypeptides, including fusion proteins, encoded by nucleic acids as described herein.

Furthermore, the subject expression vectors, by expression of CKI-insenstive CDK proteins, can be used to prevent cells in culture or in vivo from following certain differentiative pathways, and, importantly, can cause transformation of cells in culture. The ability of the mutant CDK protein to promote cell growth is particularly significant in light of the observation that human cells are notoriously difficult to grow in vitro. Accordingly, such reagents are therefore useful for transforming, and in certain instances, immortalizing, cells from primary cell cultures.

This invention also pertains to a host cell transfected with a recombinant CDK gene in order to express a mutant CDK polypeptide of the present invention. The host cell may be any prokaryotic or eukaryotic cell. For example, a mutant CDK protein of the present invention may be expressed in bacterial cells such as E. coli, insect cells (baculovirus), yeast, or mammalian cells. Other suitable host cells are known to those skilled in the art.

The term "recombinant protein" refers to a protein of the present invention which is produced by recombinant DNA techniques, wherein generally DNA encoding the mutant CDK protein is inserted into a suitable expression vector which is in turn used to transform a host cell to produce the heterologous protein.

The present invention further pertains to methods of producing the subject CKI-insensitive CDK proteins. For example, a host cell transfected with expression vector encoding one of the subject CDK protein can be cultured under appropriate conditions to allow expression of the polypeptide to occur. The polypeptide, by addition of signal sequence, may be secreted and isolated from a mixture of cells and medium containing the peptide. Alternatively, the polypeptide may be retained cytoplasmically and the cells harvested, lysed and the protein isolated. A cell culture includes host cells, media and other byproducts. Suitable media for cell culture are well known in the art. The CDK polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for particular epitopes of the subject CDK proteins. In a preferred embodiment, the mutant CDK protein is a fusion protein containing a domain which facilitates its purification, such as a CDK4-GST or CDK6-GST fusion protein.

Thus, a nucleotide sequence derived from the cloning of a CDK protein of the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. wild-type CDK proteins, p53, Rb and the like. Similar procedures, or modifications thereof, can be employed to prepare recombinant CDK proteins, or portions thereof, by microbial means or tissue-culture technology in accord with the subject invention.

A recombinant CDK protein can be produced by ligating the cloned gene, or a portion thereof, into a vector suitable for expression in eukaryotic cells. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17. In some instances, it may be desirable to express the recombinant CDK protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known and can be adapted for generating fusion proteins with the CKI-insensitive CDK mutants. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology,* eds. Ausubel et al. John Wiley & Sons: 1992).

For certain embodiments of the invention, it will be useful to have to an antibody specifically reactive with one or more of the subject CDK proteins. For instance, antibodies which are immunoselective for a p16-insensitive CDK4, relative to a wild-type CDK4 protein, can be used in the diagnostic assays described above. For instance, by subtractive immunization techniques including neonatal tolerization (Billingham et al. (1953) *Nature* 172:603–606; Golumbeski et al. (1986) *Anal Biochem* 154:373–381; Hasek et al. (1979) *Immunol Rev* 46:3–26; Reading (1982) *J Immunol Methods* 53:261–291; and Streilen et al. (1979) *Immunol Rev* 46:125–146) or chemical immunosuppression (Ahmed et al. (1984) *J Am Acad Dermatol* 11: 1115–1126; Matthew et al. (1983) *CSH Symp Quant Biol* 48:625–631; Matthew et al. (1987) *J Immunol Methods* 100:73–82; and Turk et al. (1972) *Immunology* 23:493–501), a host animal can be rendered tolerant for epitopes on the wild-type CDK. Subsequent immunization with a mutant CDK will enhance the relative number of B cells which produce antibodies specific for epitopes unique to the mutant CDK.

Monoclonal antibodies can be made using standard methods, for example, by using peptides based on the mutated sequence. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of the protein represented by amino acids 22–32 of wild type or mutant CDK4 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-CDK antisera can be obtained and, if desired, polyclonal anti-CDK antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), as the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the CDK-protein of interest and the monoclonal antibodies isolated.

The term antibody as used herein is intended to include fragments thereof which are also specifically reactive with a CDK-protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules.

Antibodies which are specifically immunoreactive with either wild type or mutant CDK proteins of the present invention can be used in immunohistochemical staining of tissue samples in order to evaluate the presence of particular mutant CDK proteins. Anti-CDK antibodies can be used diagnostically in immuno-precipitation and immunoblotting to detect and evaluate levels of one or more CDK-proteins in tissue or cells isolated from a bodily fluid as part of a clinical testing procedure. For instance, such measurements can be useful in predictive valuations of the onset or progression of tumors. Likewise, the ability to monitor certain CDK-protein levels in an individual can allow determination of the efficacy of a given treatment regimen for an individual afflicted with such a disorder. Diagnostic assays using anti-CDK, can include, for example, immunoassays designed to aid in early diagnosis of a neoplastic or hyperplastic disorder, e.g. the presence of cancerous cells in the sample, e.g. to detect cells in which a lesion of a CDK gene has occurred.

IV. Tumor Vaccines

Yet another aspect of the present invention relates to the modification of tumor cells, and/or the immune response to tumor cells in a patient by administering a vaccine to enhance the anti-tumor immune response in a host. The present invention provides, for examples, tumor vaccines based on administration of expression vectors encoding a mutant CDK protein, or portion thereof, or immunogenic preparations of polypeptides derived from mutant CDK.

In general, it is noted that malignant transformation of cells is commonly associated with phenotypic changes. Such changes can include loss, gain, or alteration in the level of expression of certain proteins. It has been observed that in some situations the immune system may be capable of recognizing a tumor as foreign and, as such, mounting an immune response against the tumor (Kripke, M., *Adv. Cancer Res.* 34, 69–75 (1981)). This hypothesis is based in part on the existence of phenotypic differences between tumor cells and normal cells, which is supported by the identification of tumor associated antigens (TAAs) (Schreiber, H., et al. *Ann. Rev. Immunol.* 6, 465–483 (1988)). TAAs are thought to distinguish a transformed cell from its normal counterpart. For example, three genes encoding TAAs expressed in melanoma cells, MAGE-1, MAGE-2 and MAGE-3, have recently been cloned (van der Bruggen, P., et al. *Science* 254, 1643–1647 (1991)). That tumor cells under certain circumstances can be recognized as foreign is also supported by the existence of T cells which can recognize and respond to tumor associated antigens presented by MHC molecules. Such TAA-specific T lymphocytes have been demonstrated to be present in the immune repertoire and are capable of recognizing and stimulating an immune response against tumor cells when properly stimulated in vitro (Rosenberg, S. A., et al. *Science* 233, 1318–1321 (1986); Rosenberg, S. A. and Lotze, M. T. *Ann. Rev. Immunol.* 4, 681–709 (1986)). In the case of melanoma cells both the tyrosinase gene (Brichard, V., et al. *J. Exp. Med.* 178:489 (1993)) and the Melan-A gene (Coulie et al. *J. Exp. Med.* 180:35)) have been identified as genes coding for antigens recognized by autologous CTL on melanoma cells.

Induction of T lymphocytes is a critical initial step in a host's immune response. Activation of T cells results in cytokine production, T cell proliferation, and generation of T cell-mediated effector functions. T cell activation requires an antigen-specific signal, often called a primary activation signal, which results from stimulation of a clonally-distributed T cell receptor (TcR) present on the surface of the T cell. This antigen-specific signal is usually in the form of an antigenic peptide bound either to a major histocompatibility complex (MHC) class I protein or an MHC class II protein present on the surface of an antigen presenting cell (APC). CD4+, helper T cells recognize peptides associated with class II molecules which are found on a limited number of cell types, primarily B cells, monocytes/macrophages and dendritic cells. In most cases class II molecules present peptides derived from proteins taken up from the extracellular environment. In contrast, CD8+, cytotoxic T cells (CTL) recognize peptides associated with class I molecules. Class I molecules are found on almost all cell types and, in most cases, present peptides derived from endogenously synthesized proteins. For a review see Germain, R., *Nature* 322, 687–691 (1986).

The importance of T cells in tumor immunity has several implications which are important in the development of anti-tumor vaccines. Since antigens are processed and presented before they are recognized by T cells, they may be derived from any protein of the tumor cell, whether extracellular or intracellular. In addition, the primary amino acid sequence of the antigen is more important than the three-dimensional structure of the antigen. Tumor vaccine strategies may use the tumor cell itself as a source of antigen, or may be designed to enhance responses against specific gene products. (Pardoll, D. 1993. *Annals of the New York Academy of Sciences* 690:301).

As detailed in the appended examples, we have identified a novel antigen which is recognized by CTL in the context of the MHC class I antigen HLA-A2. Accordingly, the present invention provides for various tumor vaccination methods and reagents which can be used to elicit an anti-tumor response against transformed cells which express/display a mutant CDK, or which have been engineered to present an antigen of a mutant CDK. In general, the tumor vaccine strategies of the present invention fall into two categorie: (1) strategies that use the tumor cell itself as a source of tumor antigen, and (2) antigen-specific vaccine strategies that are designed to generate immune responses against specific antigens of mutant CDKs.

In general, a CDK vaccine polypeptide will include at least a portion of the CDK polypeptide including a site of mutation which, when occurring in the full-length protein, results in loss of CKI-binding activity. Where the CDK tumor vaccine comprises a sufficient portion of a mutant CDK protein to otherwise provide a catalytically competent kinase subunit, the CDK protein can be further mutated to render the vaccine polypeptide catalytically inactive, e.g., by mutation of the active site lysine.

In one embodiment, a tumor cell which otherwise does not express a mutant CDK can be rendered immunogenic as a target for CTL recognition by association of a CDK vaccine polypeptide. For example, this can be accomplished by the use of gene transfer vectors. Such gene transfer vectors may be administered in any biologically effective carrier, e.g. any formulation or composition capable of effectively delivering the CDK vaccine gene to cells in vivo. Alternatively, cells from the patient or other host organism can be transfected with the tumor vaccine construct ex vivo, allowed to express the CDK protein, and, preferably after inactivation by radiation or the like, administered to an individual. In particular, viral vectors represent an attractive method for delivery of tumor vaccine antigens because viral proteins are expressed de novo in infected cells, and are degraded within the cytosol, and are transported to the endoplasmic reticulum where the degraded peptide products associate with MHC class I molecules before display on the cell surface (Spooner et al. (1995) *Gene Therapy* 2:173).

Approaches include insertion of the subject gene into viral vectors including recombinant retroviruses, adenovirus, adeno-associated virus, vaccinia virus, and herpes simplex virus-1, or plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene transfer, choice of the particular gene delivery system will depend on such factors as the phenotype of the intended target and the route of administration, e.g. locally or systemically.

Retrovirus vectors and adeno-associated virus vectors are generally understood to be the recombinant gene delivery system of choice for the transfer of exogenous genes in vivo, particularly into humans, and are accordingly preferred as the vector for delivery of the mutant CDK vaccine. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including melanocytes, both in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the CDK vaccine gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584).

Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted CDK gene can be under control of, for example, the E1A promoter, the major late promoter (MLP) and associated leader sequences, the E3 promoter, or exogenously added promoter sequences.

Yet another viral vector system useful for delivery of one of the subject mutant CDK genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In a preferred embodiment recombinant vaccinia virus is used for expression of the peptide of the present invention. This vector has the advantage of having a large capacity for genetic insertion in addition to strong promoters which allow high levels of gene expression. Infection with recombinant vaccinia viruses has been shown to protect animals from subsequent challenge with tumor cells containing tumor specific peptides (Lathe et al. 1987. *Nature* 326:878 and Meneguzzi et al. 1991. *Virology* 181:62).

In addition to viral transfer methods, such as those illustrated above, non-viral methods can also be employed to cause expression of a subject CDK polypeptide in the tissue of an animal in order to ellicit a cellular immune response. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the vaccine gene by the targeted cell. Exemplary gene delivery systems of this type include liposomal derived systems, poly-lysine conjugates, and artificial viral envelopes.

In yet another embodiment, plasmids are used to induce tumor-specific immune responses. Plasmid DNA has been used as a vaccine and has been shown to stimulate responses by both MHC class I and class II restricted T cells (reviewed in Spooner et al. supra; Conry et al. 1995 *Cancer Research* 55:1397). In other embodiments it will be desirable to use mRNA for gene therapy applications to eliminate the possibility of integration into the host genome, and thereby eliminate the potential for malignant transformation of cells (Conry et al. supra).

In another embodiment the mutant CDK peptides of the present invention may be directly delivered to the patient. Although such expression constructs as exemplified above have been shown to be an efficient means by which to obtain expression of peptides in the context of class I molecules, vaccination with isolated peptides has also been shown to result in class I expression of the peptides in some cases. For example, the use of synthetic peptide fragments containing CTL epitopes which are presented by class I molecules has been shown to be an effective vaccine against infection with lymphocytic choriomeningitis virus (Schultz et al. 1991. *Proc. Natl. Acad. Sci. USA* 88:2283) or sendai virus (Kast et al. 1991. *Proc Natl Acad Sci.* 88:2283). Subcutaneous administration of a CTL epitope has also been found to render mice resistant to challenge with human papillomavirus 16-transformed tumor cells (Feltkamp et al. (1993) *Eur. J. Immunol.* 23:2242–2249). It is contemplated that such peptides may be presented in the context of tumor cell class I antigens or by other, host-derived class I bearing cells (Huang et al. 1994. *Science* 264:961).

The mutant CDK proteins, and portions thereof, may be used in the preparation of vaccines prepared by known techniques (c.f., U.S. Pat. Nos. 4,565,697; 4,528,217 and 4,575,495). CDK polypeptides displaying antigenic regions capable of eliciting protective immune response are selected and incorporated in an appropriate carrier. Alternatively, an antitumor antigenic portion of a CDK protein may be incorporated into a larger protein by expression of fused proteins.

The CDK antitumor vaccines above may be administered in any conventional manner, including oranasally, subcutaneously, intraperitoneally or intramuscularly. The vaccine may further comprise, as discussed infra, an adjuvant in order to increase the immunogenicity of the vaccine preparation.

In some cases it may be advantageous to couple the CDK polypeptide vaccine to a carrier, in particular a macromolecular carrier. The carrier can be a polymer to which the CDK polypeptide is bound by hydrophobic non-covalent inneraction, such as a plastic, e.g., polystyrene, or a polymer to which the polypeptide is covalently bound, such as a polysaccharide, or a polypeptide, e.g., bovine serum albumin, ovalbumin or keyhole limpet hemocyanin. The carrier should preferably be non-toxic and non-allergenic. The CDK polypeptide may be multivalently coupled to the macromolecular carrier as this provides an increased immunogenicity of the vaccine preparation. It is also contemplated that the CDK polypeptide may be presented in multivalent form by polymerizing the polypeptide with itself.

In addition, the vaccine formulations may also contain one or more stabilizer, exemplary being carbohydrates such as sorbitol, mannitol, starch, sucrose, dextrin, and glucose, proteins such as albumin or casein, and buffers such as alkaline metal phosphate and the like.

The inclusion of CD4+ epitopes in the tumor vaccine in order to further enhance an anti-tumor response is also within the scope of the invention. Although the mutant CDK proteins of the present invention have been found to be presented in the context of class I MHC molecules on tumor cells, in light of the above described role of T helper cells in CTL generation, in certain embodiments CD4+ cell responses will be enhanced by the additional administration of a CD4+ epitope. Desirable T helper epitopes may be identified according to algoritms known in the art (Sette et al. 1989. *Proc Nat. Acad Sci* 86:3296), and Th epitopes may be verified by their ability to induce T cell proliferation in a standard, in vitro $^3$H thymidine incorporation assay. One embodiment the invention contemplates the coadministration of peptide fragments of the CDK4 gene which are CTL epitopes and Th epitopes to patients. In certain embodiments such Th and CTL epitopes may be expressed as fusion peptides, such as the CD8+ determinant-CD4+ determinant ($TD_c$–$TD_h$) or the like (Fayolle et al. 1991. *J. Immunol.* 147:4069; Lasarte et al. 1992. *Cell Immunol.* 141:211). In a further embodiment the CD8+ epitope may be incorporated into a synthetic lipopeptide construct, comprising, for example tripalmitoil-S-glycerylcysteinyl-seryl-serine, or the like (Deres et al. 1989. *Nature* 342:561; Schild et al. *Eur. J. Immunol.* 1991. 21:2649).

In other embodiments, the tumor cell itself can be used as the source of antitumor CDK antigens. See, for review, Pardoll, D. 1993. *Annals of the New York Academy of Sciences* 690:301. For example, cells which have been identified through phenotyping as expressing a mutant CDK can be used to generate a CTL response against a tumor. For example, tumor-infiltrating lymphocytes (TILs) may be derived from tumor biopsies which have such a phenotype. Following such protocols as described by Hom et al. (1991) *J Immunotherap* 10:153, TILs can be isolated from tumor specimens and grown in the presence of interleukin-2 in order to generate oligoclonal populations of activated T-lymphocytes that are cytolytic to the tumor cells expressing the mutant CDK.

In other embodiments, whole cell vaccines can be used to treat cancer patients. Such vaccines can include, for example, irradiated autologous or allogenic tumor cells which express (endogenously or recombaintly) a mutant CDK polypeptide (or fragment thereof), or lysates of such cells.

In certain embodiments it may be desirable to induce the tumor cells to express MHC class I or class II molecules, or costimulatory molecules in order to optimize T cell help and effective expansion of CTL clones specific for the mutant CDK peptides. In another embodiment CTL generation may be augmented by additionally providing immunostimulatory agents, such as cytokines or by causing tumor cells to express genes for cytokines.

For example, according to one aspect of the invention, a tumor cell expressing a mutant CDK is additionally modified to express B7-1 and/or B7-2 by transfection of the tumor cell with a nucleic acid encoding B7-1 and/or B7-2 in a form suitable for expression of B7-1 and/or B7-2 on the tumor cell surface. Alternatively, the tumor cell is modified by contact with an agent which induces or increases expression of B7-1 and/or B7-2 on the tumor cell surface. In yet another embodiment, B7-1 and/or B7-2 is coupled to the surface of the tumor cell to produce a modified tumor cell.

The ability of a molecule, such as B7-1 or B7-2, to provide a costimulatory signal to T cells can be determined, for example, by contacting T cells which have received a primary activation signal with the molecule to be tested and determining the presence of T cell proliferation and/or cytokine secretion. T cell can be suboptimally stimulated with a primary activation signal, for instance by contact with immobilized anti-CD3 antibodies or a phorbol ester. Following this stimulation, the T cells are exposed to cells expressing B7-1 and/or B7-2 on their surface and the proliferation of the T cells and/or secretion of cytokines, such as IL-2, by the T cells is determined. Proliferation and/or cytokine secretion will be increased by triggering of a costimulatory signal in the T cells. T cell proliferation can be measured, for example, by a standard $^3$H-thymidine uptake assay. Cytokine secretion can be measured, for example, by a standard IL-2 assay. See for example Linsley, P. S., et al., *J. Exp. Med.* 173, 721–730 (1991), Gimmi, C. D., et al., *Proc. Natl. Acad. Sci. USA* 88:, 6575–6579 (1991), Freeman, G. J., et al., *J. Exp. Med.* 174, 625–631, (1991).

Fragments, mutants or variants of B7-1 and/or B7-2 that retain the ability to interact with T cells, trigger a costimulatory signal and activate T cell responses, as evidenced by proliferation and/or cytokine production by T cells that have received a primary activation signal, are considered within the scope of the invention. A "fragment" of B7-1 and/or B7-2 is defined as a portion of B7-1 and/or B7-2 which retains costimulatory activity. For example, a fragment of B7-1 and/or B7-2 may have fewer amino acid residues than the entire protein. A "mutant" is defined as B7-1 and/or B7-2 having a structural change which may enhance, diminish, not affect, but not eliminate the costimulatory activity of the molecule. For example, a mutant of B7-1 and/or B7-2 may have a change in one or more amino acid residues of the protein. A "variant" is defined as B7-1 and/or B7-2 having a modification which does not affect the costimulatory activity of the molecule. For example, a variant of B7-1 and/or B7-2 may have altered glycosylation or may be a chimeric protein of the costimulatory molecule and another protein.

Tumor cells which express mutant forms of a CDK protein can be modified ex vivo to express B7-21 and/or B7-2 by transfection of isolated tumor cells with a nucleic acid encoding B7-1 and/or B7-2 in a form suitable for expression of the molecule on the surface of the tumor cell. The terms "transfection" or "transfected with" refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al. (*Molecular Cloning: A Laboratory Manual, 2nd Edition,* Cold Spring Harbor Laboratory press (1989)) and other laboratory textbooks. The nucleic acid to be introduced may be, for example, DNA encompassing the gene(s) encoding B7-1 and/or B7-2, sense strand RNA encoding B7-1 and/or B7-2 or a recombinant expression vector containing a cDNA encoding B7-1 and/or B7-2. The nucleotide sequence of a cDNA encoding human B7-1 and B7-2 are known in the art.

The nucleic acid is "in a form suitable for expression" in which the nucleic acid Another aspect of this invention features further modification the subject tumor cells to express one or more MHC molecules on their surface to trigger a primary, antigen-specific, signal in T cells to the mutant CDK. Before modification, tumor cells may be unable to express MHC molecules, may fail to express MHC molecules although they are capable of expressing such molecules, or may express insufficient amounts of MHC molecules on the tumor cell surface to cause T cell activation. Tumor cells can be modified to express either MHC class I or MHC class II molecules, or both. One approach to modifying tumor cells to express MHC molecules is to transfect the tumor cell with one or more nucleic acids encoding one or more MHC molecules. Alternatively, an agent which induces or increases expression of one or more MHC molecules on tumor cells can be used to modify tumor cells.

One embodiment of the invention is a modified tumor cell which expresses one or more MHC class II molecules on their cell surface. MHC class II molecules are cell-surface $\alpha/\beta$ heterodimers which structurally contain a cleft into which antigenic peptides bind and which function to present bound peptides to the antigen-specific TcR. Multiple, different MHC class II proteins are expressed on professional APCs and different MHC class II proteins bind different antigenic peptides. Expression of multiple MHC class II molecules, therefore, increases the spectrum of antigenic peptides that can be presented by an APC or by a modified tumor cell. The $\alpha$ and $\beta$ chains of MHC class II molecules are encoded by different genes. For instance, the human MHC class II protein HLA-DR is encoded by the HLA-DR$\alpha$ and HLA-DR$\beta$ genes. Additionally, many polymorphic alleles of MHC class II genes exist in human and other species. T cells of a particular individual respond to stimulation by antigenic peptides in conjunction with self MHC molecules, a phenomenon termed MHC restriction. In addition, certain T cells can also respond to stimulation by polymorphic alleles of MHC molecules found on the cells of other individuals, a phenomenon termed allogenicity. For a review of MHC class II structure and function, see Germain and Margulies, *Ann. Rev. Immunol.* 11: 403–450, 1993.

Another embodiment of the invention is a modified tumor cell which expresses one or more MHC class I molecules on the cell surface. Similar to MHC class II genes, there are multiple MHC class I genes and many polymorphic alleles of these genes are found in human and other species. Like MHC class II proteins, class I proteins bind peptide fragments of antigens for presentation to T cells. A functional cell-surface class I molecule is composed of an MHC class I $\alpha$ chain protein associated with a $\beta$2-microglobulin protein.

Tumor cells can be modified ex vivo to express one or more MHC class II molecules by transfection of isolated tumor cells with one or more nucleic acids encoding one or more MHC class II $\alpha$ chains and one or more MHC class II $\beta$ chains in a form suitable for expression of the MHC class II molecules(s) on the surface of the tumor cell. Both an $\alpha$ and a $\beta$ chain protein must be present in the tumor cell to form a surface heterodimer and neither chain will be expressed on the cell surface alone. The nucleic acid sequences of many murine and human class II genes are known. For examples see Hood, L., et al. *Ann. Rev. Immunol.* 1, 529–568 (1983) and Auffray, C. and Strominger, J. L., *Advances in Human Genetics* 15, 197–247 (1987). Preferably, the introduced MHC class II molecule is a self MHC class II molecule. Alternatively, the MHC class II molecule could be a foreign, allogeneic, MHC class II molecule. A particular foreign MHC class II molecule to be introduced into tumor cells can be selected by its ability to induce T cells from a tumor-bearing subject to proliferate and/or secrete cytokines when stimulated by cells expressing the foreign MHC class II molecule (i.e. by its ability to induce an allogeneic response). The tumor cells to be transfected may not express MHC class II molecules on their surface prior to transfection or may express amounts insufficient to stimulate a T cell response. Alternatively, tumor cells which express MHC class II molecules prior to transfection can be further transfected with additional, different MHC class II genes or with other polymorphic alleles of MHC class II genes to increase the spectrum of antigenic fragments that the tumor cells can present to T cells.

Fragments, mutants or variants of MHC class II molecules that retain the ability to bind peptide antigens and activate T cell responses, as evidenced by proliferation and/or lymphokine production by T cells, are considered within the scope of the invention. A preferred variant is an MHC class II molecule in which the cytoplasmic domain of either one or both of the $\alpha$ and $\beta$ chains is truncated. It is known that truncation of the cytoplasmic domains allows peptide binding by and cell surface expression of MHC class II molecules but prevents the induction of endogenous B7 expression, which is triggered by an intracellular signal generated by the cytoplasmic domains of the MHC class II protein chains upon crosslinking of cell surface MHC class II molecules. Kuolova. L., et al., *J. Exp. Med* 173, 759–762 (1991); Nabavi, N., et al. *Nature* 360, 266–268 (1992). Expression of costimulatory molecules is also induced by crosslinking surface MHC class II molecules, and thus truncation of MHC class II molecules may also prevent induction of B7. In tumor cells transfected to constitutively express B7-1 and/or B7-2, it may be desirable to inhibit the expression of endogenous costimulatory molecules, for instance to restrain potential downregulatory feedback mechanisms. Transfection of a tumor cell with a nucleic acid(s) encoding a cytoplasmic domain-truncated form of MHC class II $\alpha$ and $\beta$ chain proteins would inhibit endogenous B7 expression and possibly also endogenous B7-1 and B7-2 expression. Such variants can be produced by, for example, introducing a stop codon in the MHC class II chain gene(s) after the nucleotides encoding the transmembrane spanning region. The cytoplasmic domain of either the $\alpha$ chain or the $\beta$ chain protein can be truncated, or, for more complete inhibition of B7-1 (and possibly B7-2) induction, both the $\alpha$ and $\beta$ chains can be truncated. See e.g. Griffith et al., *Proc. Natl. Acad. Sci. USA* 85: 4847–4852, (1988), Nabavi et al., *J. Immunol.* 142: 1444–1447, (1989).

Tumor cells can be modified to express an MHC class I molecule by transfection with a nucleic acid encoding an MHC class I $\alpha$ chain protein. For examples of nucleic acids see Hood, L., et al. *Ann. Rev. Immunol.* 1, 529–568 (1983) and Auffray, C. and Strominger, J. L., *Advances in Human Genetics* 15, 197–247 (1987). Optionally, if the tumor cell does not express $\beta$-2 microglobulin, it can also be transfected with a nucleic acid encoding the $\beta$-2 microglobulin protein. For examples of nucleic acids see Gussow, D., et al., *J. Immunol.* 139, 3132–3138 (1987) and Pames, J. R., et al., Proc. Natl. Acad. Sci. USA 78, 2253–2257 (1981). As for MHC class II molecules, increasing the number of different MHC class I genes or polymorphic alleles of MHC class I genes expressed in a tumor cell can increase the spectrum of antigenic fragments that the tumor cells can present to T cells.

When a tumor cell is transfected with nucleic acid which encodes more than one molecule, for example a B7-2 and/or B7-3 molecule(s), an MHC class II α chain protein and an MHC class II β chain protein, the transfections can be performed simultaneously or sequentially. If the transfections are performed simultaneously, the molecules can be introduced on the same nucleic acid, so long as the encoded sequences do not exceed a carrying capacity for a particular vector used. Alternatively, the molecules can be encoded by separate nucleic acids. If the transfections are conducted sequentially and tumor cells are selected using a selectable marker, one selectable marker can be used in conjunction with the first introduced nucleic acid while a different selectable marker can be used in conjunction with the next introduced nucleic acid.

The expression of MHC molecules (class I or class II) on the cell surface of a tumor cell can be determined, for example, by immunoflourescence of tumor cells using fluorescently labeled monoclonal antibodies directed against different MHC molecules. Monoclonal antibodies which recognize either non-polymorphic regions of a particular MHC molecule (non-allele specific) or polymorphic regions of a particular MHC molecule (allele-specific) can be used and are known to those skilled in the art.

Another approach to modifying a tumor cell ex vivo to express MHC molecules on the surface of a tumor cell is to use an agent which stimulates expression of MHC molecules in order to induce or increase expression of MHC molecules on the tumor cell surface. For example, tumor cells can be contacted with the agent in vitro in a culture medium. An agent which stimulates expression of MHC molecules may act, for instance, by increasing transcription of MHC class I and/or class II genes, by increasing translation of MHC class I and/or class II mRNAs or by increasing stability or transport of MHC class I and/or class II proteins to the cell surface. A number of agents have been shown to increase the level of cell-surface expression of MHC class II molecules. See for example Cockfield, S. M. et al., *J. Immunol.* 144, 2967–2974 (1990); Noelle, R. J. et al. *J. Immunol.* 137, 1718–1723 (1986); Mond, J. J., et al., *J. Immunol.* 127, 881–888 (1981); Willman, C. L., et al. *J. Exp. Med.,* 170, 1559–1567 (1989); Celada, A. and Maki, R. *J. Immunol.* 146, 114–120 (1991) and Glimcher, L. H. and Kara, C. J. *Ann. Rev. Immunol.* 10, 13–49 (1992) and references therein. These agents include cytokines, antibodies to other cell surface molecules and phorbol esters. One agent which upregulates MHC class I and class II molecules on a wide variety of cell types is the cytokine interferon-γ. Thus, for example, in addition to treatment with the tumor vaccine of the present invention, tumor cells may be modified to increase expression of MHC molecules by contact with interferon-γ.

Another agent which can be used to induce or increase expression of an MHC molecule on a tumor cell surface is a nucleic acid encoding a transcription factor which upregulates transcription of MHC class I or class II genes. Such a nucleic acid can be transfected into the tumor cell to cause increased transcription of MHC genes, resulting in increased cell-surface levels of MHC proteins. MHC class I and class II genes are regulated by different transcription factors. However, the multiple MHC class I genes are regulated coordinately, as are the multiple MHC class II genes. Therefore, transfection of a tumor cell with a nucleic acid encoding a transcription factor which regulates MHC gene expression may increase expression of several different MHC molecules on the tumor cell surface. Several transcription factors which regulate the expression of MHC genes have been identified, cloned and characterized. For example, see Reith, W. et al., *Genes Dev.* 4, 1528–1540, (1990); Liou, H.-C., et al., *Science* 247, 1581–1584 (1988); Didier, D. K., et al., *Proc. Natl. Acad. Sci. USA* 85, 7322–7326 (1988).

In clinical settings, the therapeutic compound of the present invention can be introduced into a patient by any of a number of methods, each of which is familiar in the art. For instance, a pharmaceutical preparation of the gene delivery system or peptide can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle or peptide can be introduced by catheter (see U.S. Pat. No. 5,328,470) or by stereotactic injection (e.g. Chen et al. (1994) *PNAS* 91: 3054–3057). A vaccine gene can be delivered in a gene therapy construct by electroporation using techniques described, for example, by Dev et al. ((1994) *Cancer Treat Rev* 20:105–115).

The pharmaceutical preparation of the vaccine therapy construct or peptide can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral or adenoviral vectors, the pharmaceutical preparation can comprise one or more cells which produce the gene delivery system.

Suitable pharmaceutical vehicles for administration to a patient are known to those skilled in the art. For parenteral administration, the CDK immunogen will usually be dissolved or suspended in sterile water or saline. For enteral administration, the immunogen will be incorporated into an inert carrier in tablet, liquid, or capsular form. The preparation may also be emulsified or the active ingredient encapsulated in liposome vehicles. The composition or formulation to be administered will, in any event, contain a quantity of the CDK polypeptide adequate to achieve the desired immunized state in the subject being treated. The immunogen preparations according to the invention may also contain other peptides or other immunogens.

Suitable carriers may be starches or sugars and include lubricants, flavorings, binders, and other materials of the same nature. For instance, the immunogen can be formulated as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-trialkyl and aryl amines and substituted ethanolamines.

The immunogen, which may be coupled to a carrier, is preferably administered after being mixed with immunization adjuvants. Conventional adjuvants include, for example, complete or incomplete Freund's adjuvant, aluminum hydroxide, Quil A, EMA, DDA, TDM-Squalene, lecithin, alum, saponin, and such other adjuvants as are well known to those in the art, and also mixtures thereof. For example, the CDK immunogen may be mixed with the N-butyl ester (murabutide) of the muramyl dipeptide (MDP; N-acetyl-glucosamine-3-yl-acetyl-L-alanyl-D-isoglutamine) diluted in a saline solution. The mixture may then be emulsified by means of an equal volume of squalene in the presence of arlacel (excipients). It is also possible to use other adjuvants such as analogues of MDP, bacterial fractions such as streptococcal preparations (OK 432), Biostim (01K2) or modified lipopolysaccharide preparations (LPS), peptidoglycans (N-Opaca) or proteoglycans (K-Pneumonia). In the case of these excipients, water-in-oil emulsions are preferable to oil-in-water emulsions.

The use of the instant invention is predicted to be of benefit in the treatment of any type of tumor which harbors a mutant CDK4 gene. For example, treatment of tumors of the lung, breast, brain, bone, skin, bladder, kidney, ovary, or lymphocytes is contemplated. In a preferred embodiment the tumor vaccine of the present invention is used to treat melanoma.

In addition to enhancing the immune response againes a tumor at its original site, the tumor cell vaccine of the current invention may also be used in a method for preventing or treating metastatic spread of a tumor or preventing or treating recurrence of a tumor. Thus, administration of modified tumor cells or modification of tumor cells in vivo as described herein can provide tumor immunity against cells of the original, unmodified tumor as well as metastases of the original tumor or possible regrowth of the original tumor.

As demonstrated in the appended Examples, subjects develop an anti-tumor specific T cell response which is specific for mutant forms of CDK proteins and is effective in keeping the patients disease free. Thus, the subject develops anti-tumor specific immunity. It is also contemplated that the invention may be useful in inducing immunity to tumors in succeptible individuals before they arrise, for example in the case of familial malignancies. A strong hereditary component has been identified for certain types of malignancies, for example certain breast and colon cancers and in susceptability to melanoma. In families with a known susceptibility to a particular malignancy and in which one individual presently has a tumor bearing a mutant CDK protein, peptides presented by class I molecules of these patients could be administered to susceptible, histocompatible family members to induce an anti-tumor response in the recipient against the type of tumor to which the family is susceptible. This anti-tumor response could provide protective immunity to subsequent development of a tumor in the immunized recipient.

Exemplification

The invention now being generally described, it will be more readily understood by reference to the following examples which are included merely for purposes of illustration of certain aspects and embodiments of the present invention, and are not intended to limit the invention.

EXAMPLE 1

This example describes the identification of a CDK4 mutation and the role of mutant CDK in modulating the immune response.

Tumor antigens have been demonstrated in murine tumors induced by chemicals and ultraviolet (UV) light (R. T. Prehn and J. M. Main, J. Natl. Cancer Inst. 18, 769 (1957); P. J.Srivastava, et al. Proc. Natl. Acad. Sci. U.S.A. 84, 3807 (1987); P. L. Ward, et al., J. Exp. Med. 170, 217(1989)). CTLs mediate the rejection of these experimental tumors, and their target antigens have been identified in some instances (B. Van den Eynde, et al. J. Exp.Med. 173, 1373 (1991); O. Mandelboim et al., Nature 369, 67 (1994); V. de Bergeyck, et. al., Eur. J. Immunol. 24, 2203 (1994); A. Uenaka et al., J. Exp. Med. 180, 1599 (1994)). Human tumors have also been examined for equivalent antigens (Reviewed in D. M. Pardoll, Nature 369, 357 (1994)). In the human melanoma model of patient SK29(AV), the response of blood-derived lymphocytes to autologous cultured tumor cells has been studied over a long period (P. O. Livingston, et al., Int. J. Cancer 24, 34 (1979); A. Knuth, et al., Proc. Natl. Acad. Sci. U.S.A. 81, 3511 (1984); T. Wolfel et al., Int. J. Cancer 55, 237 (1993)). Some autologous tumorreactive CTL clones were broadly cross-reactive and were found to recognize melanocyte differentiation antigens such as tyrosinase and Melan-A/MART-1 (V. Brichard et al., J. Exp. Med. 178, 489 (1993); P. Coulie et al.,ibid. 180, 35 (1994)). However, HLA-A2-restricted CTLs against a third antigen, called SK29-C, lysed only autologous tumor cells but did not recognize autologous Epstein-Barr virus-transformed B lymphocytes or a panel of allogeneic HLA-A2-positive melanoma cell lines. Three HLA-A2-restricted CTL clones recognizing SK29-C CTLs requiring antigen SK29-C (CTL anti-C) were isolated from lymphocytes separated from the patient's blood in different years and were used in our experiments here (Clones CTL3/7 and CTL5/76 were isolated from peripheral blood of patient SK29(AV) drawn in 1982 and clone CTL14/35 from blood drawn in 1987.).

Figure 1A:
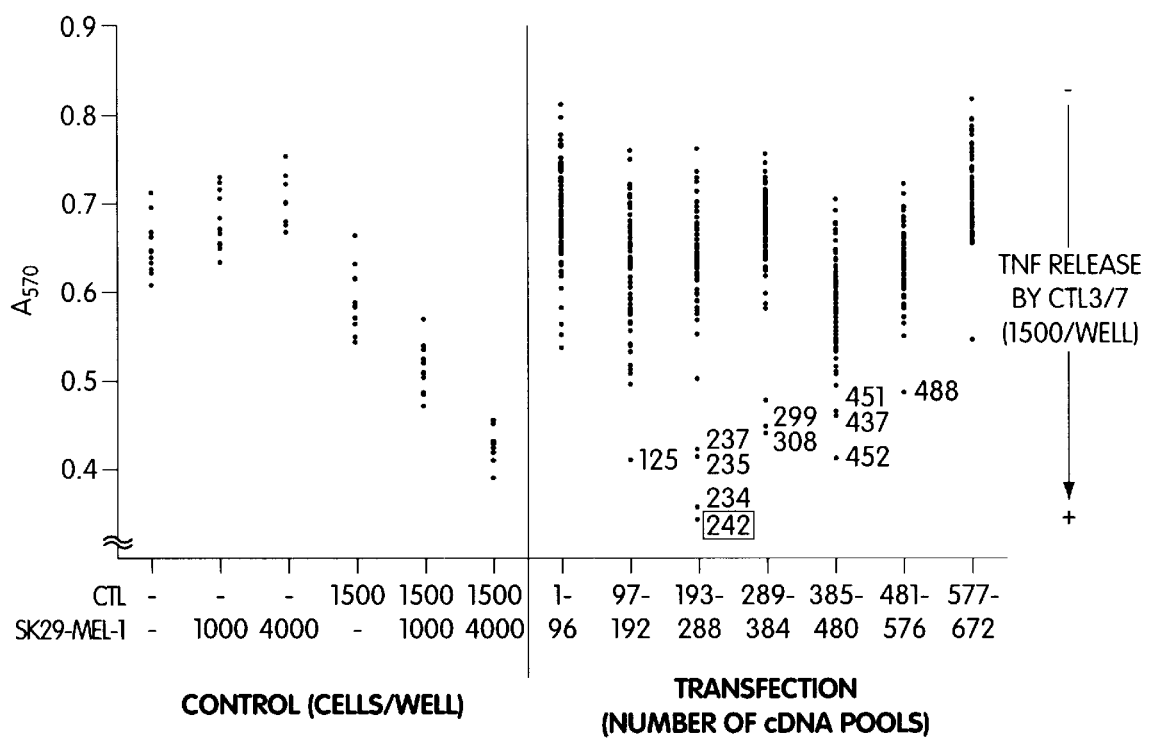
FIGS. 1A and 1B a graphs illustrating the identification of cDNAs encoding the melanoma antigen SK29-C.
Figure 1B:
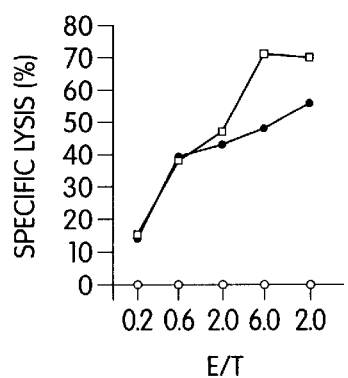

Using the COS transfection approach for cloning T cell-defined antigens (V. Brichard et al., J. Exp. Med. 178, 489 (1993); P. Coulie et al., ibid. 180, 35 (1994)), we identified SK29-derived complementary DNA (cDNA) pools that induced the production of tumor necrosis factor (TNF) by CTL anti-C after cotransfection with HLA-A*0201 (FIG. 1A). Positive pool 242 was cloned. Four of 1920 clones derived from pool 242 induced TNF production, and one of them, C11.1, was chosen for further experiments. C11.1 also conferred recognition by CTLs in direct cytotoxicity testing when stably transfected into allogeneic melanoma cells expressing HLA-A2.1 (FIG. 1B). This result largely excluded the possibility that the high-level replication of C11.1 in COS cells generated an artificial CTL target that would not be produced under moderate expression conditions.

Clone C11.1 contained a cDNA insert 1331 base pairs (bp) (The full sequence of the cDNA insert of clone C11.1 is available from the European Molecular Biology Laboratory nucleotide sequence database (accession number Z48970). Sequence analysis was performed with the program. GeneWorks on GenBank release 86.) whose longest open reading frame encoded a 303-amino acid protein. This protein is identical in sequence to human cyclin-dependent kinase 4 (CDK4) except for an arginine (R) to cysteine (C) replacement at position 24 produced as a result of a cytosine to thymine (C right arrow T) transition (H. Matsushime et al., Cell 71, 323 (1992)). Accordingly, this mutation was named R24C and the resultant mutant protein was named CDK4-R24C.

Figure 2A:
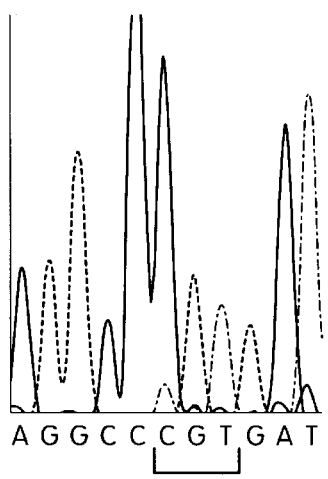
FIGS. 2A, 2B amd 2C show sequences for a CDK4 allele of SK29 melanoma with a missense mutation in codon 24 (bracketed). Genomic DNA was extracted from (FIG. 2A) the patient's Epstein-Barr virus-transformed B lymphocytes (SK29-EBV-B) and from (FIG. 2B) cultured melanoma cells (SK29-MEL-1). The cell line SK29-MEL (previously names SK-MEL-29) had been dervied from a lymph node metastasis in 1975. SK29-MEL-1 is a clone of the SK29-MEL cell line. PCR reactions were performed on extracted DNA with primers 5'-TTGAATTCGCCGCC<u>ATGGCTACCTCTCGA</u> SEQ ID NO:1 (primer C2) and 5'-AATCTAGAGCCGCC<u>TTGATCGTTTCGGCT</u> SEQ ID NO:2 (primer C3), allowing amplification of codons 1 to 117 (CDK4-specific primer sequences are underlined). Fragments amplified with these primers from both cell lines were 520 bp in length, as compared to the 353 bp expected from the CDK4 cDNA sequence; the increased length was due to the presence of an intron.
Figure 2B:
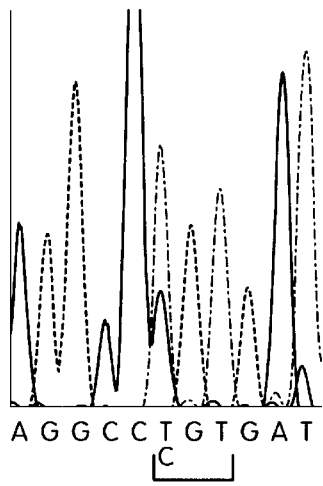
Figure 2C:
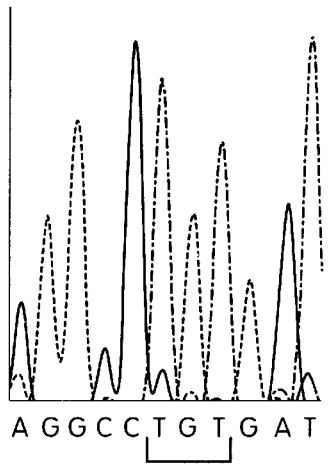

To determine if the R24C mutation was a somatic mutation, we compared CDK4 gene sequences amplified by polymerase chain reaction (PCR) from normal lymphocytes and from cultured melanoma cells of the patient. The sequence obtained with lymphocyte DNA contained a CGT codon (arginine) at position 24 (FIG. 2A), whereas the sequence obtained from melanoma cell DNA contained both CGT (arginine) and TGT (cysteine) codons at position 24, which suggests that the patient's melanoma cells carried both the wild-type and the R24C alleles (FIG. 2B). Both the mutant and the wild-type alleles were transcribed in SK29 melanoma cells. Genomic DNA was extracted from paraffin sections of a lymph node metastasis of patient SK29(AV), and CDK4 fragments around codon 24 were amplified. Direct sequencing of PCR fragments revealed that the R24C mutation was also present in the patient's metastatic tumor tissue (FIG. 2C); the amplified DNA was subsequently cloned, and after sequencing, it was found that 14 of 16 clones carried the R24C mutation, whereas the others were identical to the wild-type sequence. The predominance of the mutated CDK4 allele in the metastatic tissue may have resulted from amplification of CDK4-R24C. Amplification of the gene encoding CDK4 is a relatively frequent alteration in sarcomas and gliomas (Z. A. Khatib et al., Cancer Res. 53, 5535 (1993); J. He et al., ibid. 54, 5804 (1994); E. E. Schmidt, et al., ibid., p. 6321.).

Altogether, these results indicate that R24C is a somatic mutation. The C right arrow T transition that produced the R24C mutation occurred at a dipyrimidine site (FIG. 2). This type of mutation is typically caused by UV irradiation (D. E. Brash et al., Proc. Natl. Acad. Sci. U.S.A. 88, 10124 (1991)), a key etiologic factor in melanoma. The R24C mutation might therefore have occurred early in tumorigenesis. The same R24C mutation was found in one of 28 other melanomas that have been surveyed so far (DNA was extracted from four allogeneic melanoma lines and from paraffin-embedded melanoma tumor samples of 24 patients as described (M. Volkenandt, N. S. McNutt, A. P. Albino, J. Cutaneous Pathol. 18, 210 (1991)). A270-bp CDK4 genomic fragment was amplified with primers 5 feet— ATGGCTACCTCTCGATATGAGCCAGTG (codons 1 to 9) and 5 feet AGGCTGTCTTTTCCCTTTACTCCCCA binding to intron sequence (The intron amplified with CDK4 primers C2 and C3 (see FIG. 2A) from genomic DNA was interspersed between codons 73 and 74. Thus, the mutation in codon 24, described herein, does not affect splicing.). By using an exon-intron primer pair, contamination with cDNA was excluded. Amplified CDK4 fragments were purified and directly sequenced as shown in FIG. 2. DNA sequences from 27 of 28 melanomas were identical to that of wild-type CDK4. One melanoma tumor carried both CGT (arginine) and TGT (cysteine) codons at position 24 and therefore contained an R24C allele.).

Figure 3:
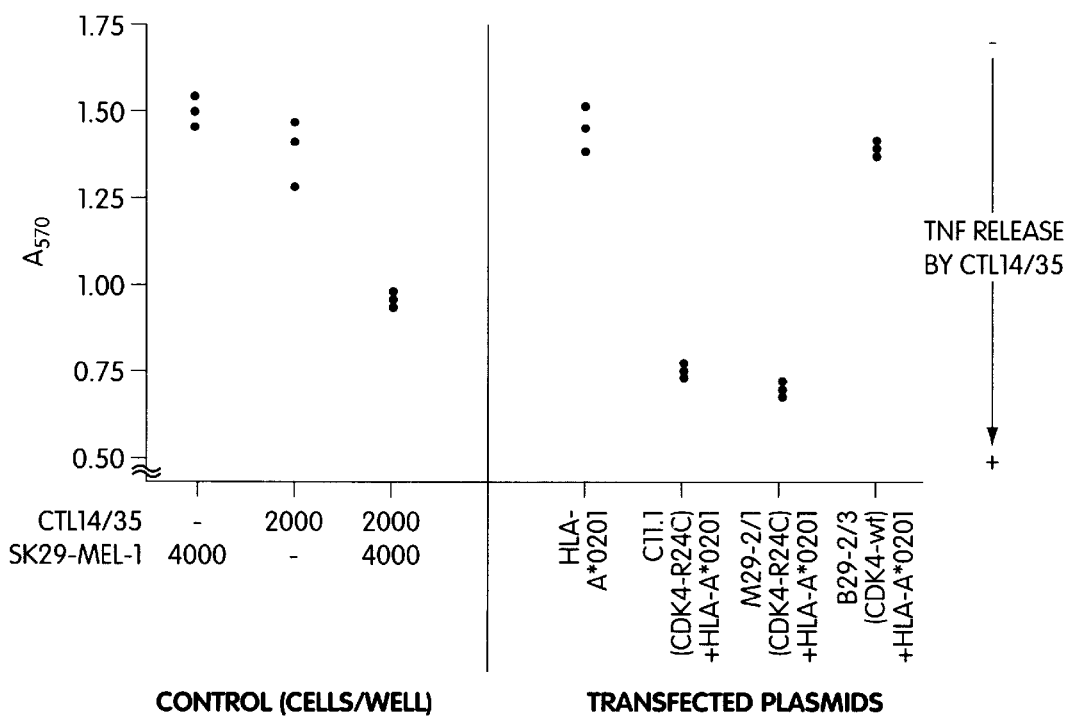
FIG. 3 illustrates the results of transfection of COS cells with mutant and wild-type CDK4 cDNA frgments and assay for recognition by CTL anti-C. CDK4 cDNA fragments spanning codons 1 to 117 were amplified by PCR after reverse transcription of DNA from the patient's lymphocytes and melanoma cells and cloned in expression vector pcDNAI/Amp. COS cells were transfected by the DEAE-dextran method, and the TNF assay was performed as shown in FIG. 1A. The cDNA clonse M29-2/1 was derived from RNA of SK29-MEL-1, and its sequence was identical to that of clone C11.1 (CDK4-R24C). The cDNA clone B29-2/3 was derived from RNA of Epstein-Barr virus-transformed B lymphocytes, and its sequence was identical to that of wild-type CDK4. COS-7 cells were cotransfected with plasmids C11.1, M29-2/1, or B29-2/3 (200 ng of each per well) and HLA-A*0201 (inserted in pcDNAI/Amp, 200 ng per well) or with HLA-A*0201 alone. Transfectants were tested for their ability to induce TNF production by CTL anti-C (CTL 14/35; 1500 cells/well). Each point indicates the result of a TNF assay with a single transfected COS cell pupulation. As a control, production of TNF in the presence of various numbers of SK29-MEL-1 cells was measured. Data were confirmed in five independent experiments.

To determine if the R24C mutation was associated with CTL recognition, we transfected mutated or wild-type CDK4 cDNA fragments together with HLA-A*0201 DNA into COS-7 cells. Whereas cDNAs encoding CDK4-R24C (M29-2/1) conferred recognition by CTL anti-C, those encoding wild-type CDK4 (B29-2/3) did not (FIG. 3). This result suggests that $Cys^{24}$ either is part of the peptide antigen recognized by CTL anti-C or influences peptide production. The selective recognition of CDK4-R24C was consistent with our earlier specificity analysis for CTL anti-C on autologous and allogeneic HLA-A2-positive target cell lines.

Figure 4:
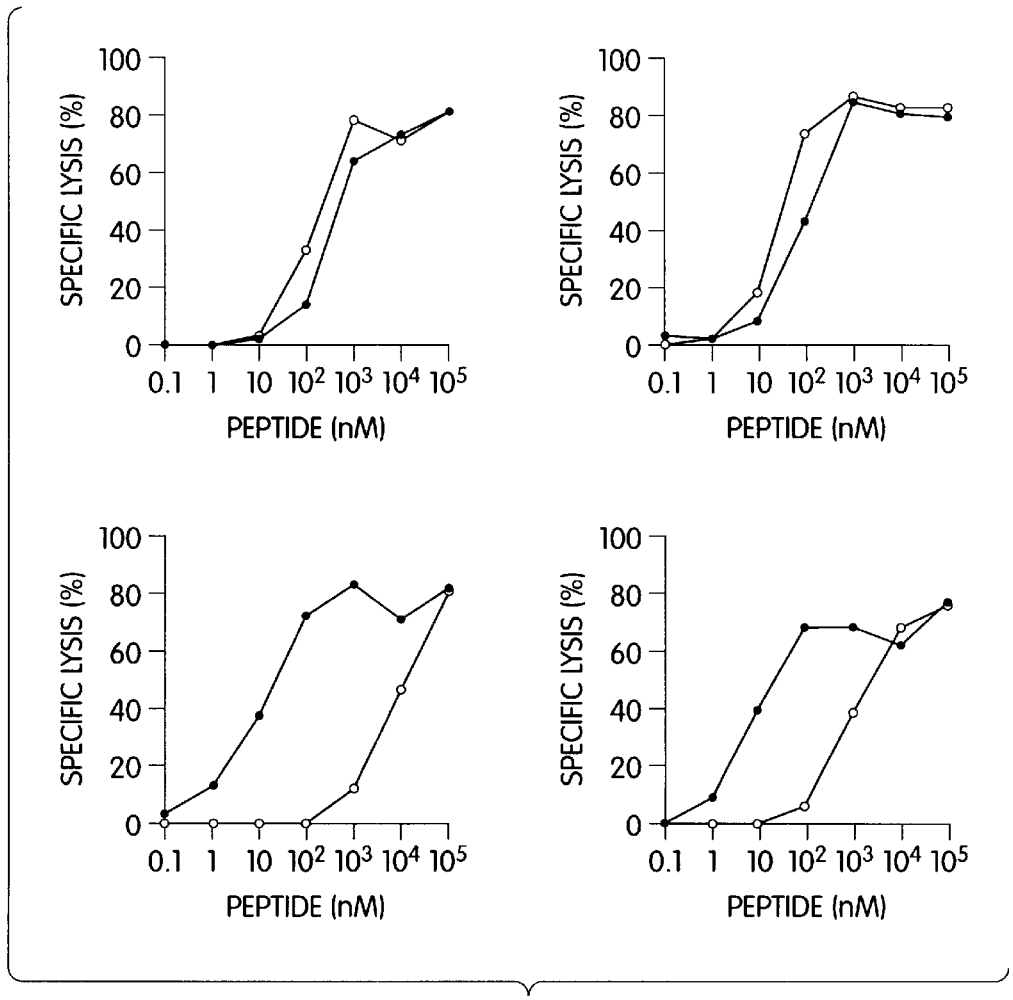
FIG. 4 is a set of graphs illustrating the recognition of synthetic CDK4 peptides by CTL anti-C. Breifly, T2 cells were labeled with Na($^{51}$Cr)O$_4$ and then incubated at a concentration of 2000 cells per well for 90 minutes with the indicated concentrations of peptides in the presence of human β$_2$ -microglobulin (10 μg/ml; Sigma). [CTL anti-C (CTL3/7, -left panels) and CTL 14/35, right panels)] was added at an effector; target ratio of 40:1. Chromium release was measured after 6 hours. Amino acid sequences were as follows: Top panels: open circles, KA<u>R</u>DPHSGHFV SEQ ID NO:6, closed circles, KA<u>C</u>DPHSGHFV SEQ ID NO:7.

To identify the CTL target peptide, we generated CDK4-R24C cDNA fragments by PCR, cotransfected them with HLA-A*0201 DNA into COS cells, and tested the transfectants for CTL recognition. These results showed that the CTL target peptide was encoded by codons 22 to 33. Synthetic peptides corresponding to amino acids 22 to 32 of mutated (R24C) and wild-type (wt) CDK4 were tested for recognition by CTL anti-C. The two peptides, $22-32^{R24C}$ and $22-32^{wt}$, sensitized target cells equally well against CTL lysis (FIG. 4). This finding was inconsistent with our earlier observation that wild-type cDNA fragments did not confer CTL recognition after transfection (FIG. 3). However, a clear difference between mutated and wild-type peptides was observed for decapeptides $23-32^{R24C}$ and $23-32^{wt}$ with respect to target sensitizing activity. Peptide $22-32^{R24C}$ induced half-maximal lysis at a concentration of 10 nM and was about two or three orders of magnitude more efficient than its wild-type homology (FIG. 4).

The affinity of exogenously added peptides for HLA-A2.1 correlates with their ability to induce the expression of HLA-A2.1 on 0.174XCEM.T2 cells (T2). We compared the two decapeptides in this assay and found that peptide $23-32^{R24C}$ increased HLA-A2.1 expression on T2 cells to an extent comparable to that of known high-affinity peptides, whereas peptide $23-32^{wt}$ had no effect. No significant lysis of target cells was induced by peptides $22-31^{R24C}$ and $24-32^{R24C}$. We conclude that $Ala^{23}$ and $Val^{32}$ serve as the N H.sub.2 -and COOH-terminal anchor residues, respectively, as in other HLA-A2.1 binding peptides, and that the R24C mutation in CDK4 enhances binding to HLA-A2.1 for peptide 23-32. Differential peptide binding affinity might account for the resistance of cells expressing wild-type CDK4 to lysis by CTL anti-C. It is also possible that in contrast to the R24C-derived peptide, the wild type-derived peptide is not presented on the cell surface, which would imply that the R24C mutation affects peptide processing or transport. A comparable situation has been discussed for the CTL-defined antigen P35B in mouse mastocytoma P815 (J.-P. Szikora, A. Van Pel, T. Boon, Immunogenetics 37, 135 (1993)).

To characterize the effect of the R24C mutation on CDK4 function, we expressed CDK4-R24C in insect cells. Cell extracts from cultures metabolically labeled with $^{35}S$ methionine and coinfected with baculoviruses encoding cyclin D1 and CDK4-R24C were mixed with similar extracts from insect cells expressing $p16^{Ink4a}$, p27, or p21, all known inhibitors of CDK4 (M. Serrano, et al., Nature 366, 704 (1993); Y. Xiong et al., ibid., p. 701; W. S. El-Deiry et al., Cell 75, 817 (1993); J. W. Harper,et al., ibid., p. 805; Y. Gu, C. W. Turek, D. O. Morgan, Nature 366, 707 (1993); A. Noda, et al., Exp. Cell Res. 211, 90 (1994); K. Polyak et al., Cell 78, 59 (1994); H. Toyoshima and T. Hunter, ibid., p. 67.). Immunoprecipitation with antibodies to CDK4 showed that CDK4-R24C formed stable complexes with cyclin D1, p27, and p21, but not with $p16^{Ink4a}$ (FIG. 5A). In kinase assays, both CDK4-wt and CDK4-R24C were enzymatically active in the presence of cyclin D1, and both were inhibited by p27 and p21 (FIG. 5B). In contrast, CDK4-R24C was considerably less sensitive to inhibition by $p16^{Ink4a}$ than was the wild-type enzyme (FIG. 5B). Similarly, $p15^{Ink4b}$, a member of the Ink4 family of inhibitors (G. J. Hannon and D. Beach, Nature 371, 257 (1994)), did not form a stable complex with CDK4-R24C and did not effectively inhibit its kinase activity. These results indicate that CDK4-R24C is selectively impaired in its interaction with $p16^{Ink4a}$ and $p15^{Ink4b}$ and suggest that $Arg^{24}$ is directly involved in binding to $p16^{Ink4a}$ and $p15^{Ink4b}$.

The cell cycle regulatory pathway that involves the retinoblastoma protein (Rb), cyclin D1, $p16^{Ink4a}$, and CDK4 has been implicated in tumorigenesis (Reviewed in T. Hunter and J. Pines, Cell 79, 573 (1994)). In particular, $p16^{Ink4a}$ can inhibit cell proliferation and oncogenic transformation of cultured cells (M. Serrano, et al., Science 267, 249 (1995); J. Lukas et al., Nature 375, 503 (1995); J. Koh, et al., ibid., p. 506.). Inactivation of the gene encoding p16$^{Ink4a}$ is common in some tumor cell lines and primary tumors and is responsible for genetic predisposition to melanoma (A. Kamb et al., Science 264, 436 (1994); T. Nobori et al., Nature 368, 753 (1994); A. Okamoto et al., Proc. Natl. Acad. Sci. U.S.A. 91, 11045 (1994); N. Hayashi et al., Biochem. Biophys. Res. Commun. 202, 1426 (1994); T. Mori et al., Cancer Res. 54, 3396 (1994); C. Caldas et al., Nature Genet. 8, 27 (1994); J. Hebert, et al., Blood 84, 4038 (1994); J. Jen et al., Cancer Res. 54, 6353 (1994); C. J. Hussusian et al., Nature Genet. 8, 15 (1994); K. Ranade et al., ibid. 10, 114 (1995)). Mutation of CDK4 at positions that disrupt its interaction with p16$^{Ink4a}$ may constitute a mechanism to subvert this regulatory pathway in tumor cells. It seems plausible that, aside from its antigenicity, the expression of CDK4-R24C contributed to malignant transformation in melanoma SK29(AV). Antigens derived from oncogenic proteins are ideally suited as targets of tumor rejection responses because tumorigenesis is likely to depend on the continued expression of the antigen. Indeed, CTLs against viral oncoproteins have been demonstrated to elicit rejection response and protective immunity to virally induced murine tumors (W. M. Kast et al., Cell 59, 603 (1989); M. C. Feltkamp et al., Eur. J. Immunol. 23, 2242 (1993)). It remains to be proven that human tumor-specific antigens like CDK4-R24C can constitute targets for rejection response in vivo. However, it should be noted that patient SK29(AV) has been free of detectable disease since 1978.

The teachings of Wölfel et al. are expressly incorporated by reference herein.

EXAMPLE 2

Further Characterization of CCR-insensitive CDK4 Mutants

We reisolated the mutant CDK4 by standard cloning of CDK4 followed by generation of a the cysteine mutation by oligonucleotide primer mutagenesis. To characterize the effect of the mutation, we compared the mutant and wild-type enzyme based on a number of different criteria, including intrinsic activity (e.g. did the mutant constitutively activate CDK4), as well as the ability of other regulatory proteins to control CDK4 activation. Briefly, we generated a series of baculovirus expression systems for over-expressing various proteins. In particular, Sf9 cell lysates (Desai et al. (1992) *Mol Cell Biol* 3:571–582) were obtained for mutant and wild-type CDK4, cyclin D1, p16, p15, p21 and p27 (see Polyak et al. (1994) *Genes Dev* 8:9–22; and Toyoshima et al. (1994) *Cell* 78:67–74). Using a GST-RB fusion protein as a substrate for detecting CDK4 kinase activity, various combinations of lysate were mixed and tested for CDK4 activation/inhibition.

When the mutant CDK4 was expressed alone in Sf9 cells, no appreciable phosphorylation of the RB substrate was detected, as is also the case with the wild-type enzyme, indicating that the mutation did cause constitutive acitvation of CDK4. Overexpression of a CDK4 and cyclin D1 in an Sf9 lysate was also identical for both mutant and wild-type kinase, as each was shown to be activated in the presence of cyclin D1. However, upon addition of increasing amounts of either p16- or p15-containing lysate to the CDK4/cyclin D mixture, the wild-type CDK4 was inhibited yet the mutant CDK4 was relatively unaffected, indicating that the mutation gave rise to kinase whose activity is insensitive to either p15 or p16. Furthermore, immunoprecipitation demonstrated that neither p15 or p16 were capable of binding the mutant, as they were apparently lost from the complex which is ordinarily seen with the wild-type CDK4. Finally, similar experiments carried out with p21 and p27 indicated that the particular mutation, Arg24-Cys, did not effect the binding or inhibitory ability of either of those proteins. An analogous mutation to Arg31 of CDK6 (SEQ ID No. 10; and Bates et al. (1994) *Oncogene* 9:71–79 for the wild-type gene) is expected to have the same effect.

Utilizing the Arg-24 residue as a reference point, we have further identified by molecular modeling other residues which may also be involved in the recognition of p16/p15. Utilizing the coordinates for CDK2 (DeBondt et al. (1993) *Nature* 363:595–602; Endicott et al. (1994) *Prot Eng* 7:243–253; and Morgan et al. (1994) *Curr Opin Cell Biol* 6:239–246)) we have constructed a model for CDK4. Focusing our attention on residues in the spatial vicinity of Arg-24 and that are conserved between CDK4 and CDK6 (but different from CDK2 or CDC2, we have recombinantly generated and analyzed a number of new CDK4 mutants for their ability to bind p16. These mutants and their p16-binding abilities are summarized in Table 1 below.

Three changes abolished the interaction with p16. When these changes were visualized onto the 3-dimensional structure, it was apparent that these residues form a cluster of four amino acid residues accessible to solvent. These residues, K22, R24, H95 and D97 define a surface in the small lobe of CDK4, in very close proximity to the ATP binding site, but far away from the cyclin binding site or the substrate binding site. This surface likely represents at least a portion of the p16/p15-recognition surface present in CDK4 (and homologously in CDK6). Accordingly, an attractive model for p16/p15 inhibition of CDK4/CDK6 provides an occlusion or distorting effect to the ATP-binding site upon binding of the CCR protein such that ATP either does not bind to CDK4 or is not properly positioned to be used as a phosphate donor.

TABLE 1 p16 binding to CDK4 mutants

| residue # | conservation | mutation | p16 binding |
|---|---|---|---|
| 7 | CDK4/CDK6 specific | E → Q | no effect |
| 10 | CDK4/CDK6 specific | A → E | no effect |
| 11 | CDK4/CDK6 specific | E → K | no effect |
| 22 | conserved in a CDKs | K → A | no binding to p16 |
| 24 | conserved in a CDKs | R → S | no binding to p16 |
| 25 | CDK4/CDK6 specific | D → N | no effect |
| 31 | CDK4/CDK6 specific | F → V | no effect |
| 78 | CDK4/CDK6 specific | C → I | no effect |
| 81 | CDK4/CDK6 specific | S → E | no effect |
| 82 to 86 | CDK4/CDK6 specific | RTDRE → N | no effect |
| 95 to 97 | CDK4/CDK6 specific | HVD → FLH | no binding to p16 |

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A diagnostic method for detecting mutation of a sample protein which disrupts binding to another target protein, comprising:
    i. isolating a gene encoding said sample protein from a sample of biopsied cells, wherein said sample of cells is suspected of containing mutational changes;
    ii. cloning said gene into a two hybrid assay to produce a host cell comprising
        (a) a reporter gene operably linked to a transcriptional regulatory sequence,
        (b) a first chimeric gene which encodes a first fusion protein, said first fusion protein including a target protein to which a wild-type form of said sample protein binds and to which binding of the cloned sample protein is to be assessed,
        (c) a second chimeric gene which encodes a second fusion protein including said cloned sample protein,
    wherein interaction of said first and second fusion proteins, if at all, is mediated by binding of said target protein and sample protein portions, and expression of said reporter gene is sensitive to interactions between said transcriptional regulatory sequence and a complex of said first and second fusion proteins;

iii. measuring expression of said reporter gene; and iv. comparing the level of expression of said reporter gene to a level of expression in a two hybrid assay having a second fusion protein comprising a wild-type form of said sample protein instead of the cloned sample protein, wherein a decrease in the level of expression is indicative of a mutation to said gene which disrupts the ability of said sample protein to bind to another cellular protein, and which correlates to the presence of a disorder.

2. The method of claim 1, wherein said target protein is a CDK-inhibitory (CKI) protein, and said sample protein is a cyclin dependent kinase (CDK).

3. The method of claim 2, wherein said target CKI protein is selected from the group consisting of p16, p15, p18, p19 and homologs thereof.

4. The method of claim 2, wherein said CDK is selected from the group consisting of CDK4 and CDK6.

5. The method of claim 2, wherein said target CKI protein is selected from the group consisting of p21, p27, p57 and homologs thereof.

6. The method of claim 1 wherein said sample protein is a CDK-inhibitory protein, and said target protein is a cyclin dependent kinase.

7. The method of claim 6, wherein said CDK-inhibitory protein is selected from the group consisting of p16, p15, p18, p19 and homologs thereof.

8. The method of claim 6, wherein said CDK is selected from the group consisting of CDK4 and CDK6.

9. The method of claim 1 wherein said sample protein is selected from the group consisting of p21, p27 and homologs thereof, and said target protein is a cyclin dependent kinase.

10. The method of claim 1, wherein one of either said sample protein or target protein is an Rb or RB-like protein.

11. The method of claim 1, wherein one of either said sample protein or target protein is a p53 protein.

* * * * *